(12) United States Patent
Adler et al.

(10) Patent No.: US 11,642,244 B2
(45) Date of Patent: May 9, 2023

(54) PHOTOACTIVATION SYSTEMS AND METHODS FOR CORNEAL CROSS-LINKING TREATMENTS

(71) Applicant: Avedro, Inc., Waltham, MA (US)

(72) Inventors: Desmond C. Adler, Bedford, MA (US); Mikhail Smirnov, North Andover, MA (US); David Usher, Waltham, MA (US); Behrouz Tavakol, Lexington, MA (US); Jason Hill, Auburndale, MA (US); Jie Zhang, Andover, MA (US); Amit Mukherjee, Acton, MA (US); Alex Yildizyan, Lexington, MA (US)

(73) Assignee: Avedro, Inc., Waltham, MA (US)

( * ) Notice: Subject to any disclaimer, the term of this patent is extended or adjusted under 35 U.S.C. 154(b) by 118 days.

(21) Appl. No.: 16/987,370

(22) Filed: Aug. 6, 2020

(65) Prior Publication Data

US 2021/0038428 A1 Feb. 11, 2021

Related U.S. Application Data

(60) Provisional application No. 62/883,197, filed on Aug. 6, 2019.

(51) Int. Cl.
*A61F 9/008* (2006.01)

(52) U.S. Cl.
CPC .... *A61F 9/008* (2013.01); *A61F 2009/00844* (2013.01); *A61F 2009/00872* (2013.01); *A61F 2009/00897* (2013.01)

(58) Field of Classification Search
CPC ............ A61F 9/008; A61F 2009/00844; A61F 2009/00897
See application file for complete search history.

(56) References Cited

U.S. PATENT DOCUMENTS

| | | |
|---|---|---|
| 4,034,750 A | 7/1977 | Seiderman |
| 4,665,913 A | 5/1987 | L'Esperance, Jr. |

(Continued)

FOREIGN PATENT DOCUMENTS

| | | |
|---|---|---|
| DE | 102008046834 | 3/2010 |
| EP | 1561440 | 8/2005 |

(Continued)

OTHER PUBLICATIONS

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).

(Continued)

*Primary Examiner* — Allen Porter
*Assistant Examiner* — Skylar Lindsey Christianson
(74) *Attorney, Agent, or Firm* — K&L Gates LLP

(57) ABSTRACT

A system for treating an eye includes a laser light source providing photoactivating light. The system includes a scanning system to receive the photoactivating light as a laser beam and to move the laser beam over a cornea treated with a cross-linking agent. The system includes a controller that provides control signal(s) to programmatically control the laser light source and the scanning system. The control signal(s) cause the laser beam to visit region(s) of the cornea more than once according to a scan pattern and expose the region(s) to the photoactivating light. The photoactivating light causes the cross-linking agent in the exposed region(s) to react with oxygen to generate cross-linking activity in the exposed region(s). The scan pattern causes a predetermined period of time to pass between visits by the laser beam to the exposed region(s), the predetermined period of time allowing oxygen in the exposed region(s) to replenish.

18 Claims, 36 Drawing Sheets

(56) References Cited

U.S. PATENT DOCUMENTS

| | | | |
|---|---|---|---|
| 4,712,543 A | 12/1987 | Baron | |
| 4,764,007 A | 8/1988 | Task | |
| 4,891,043 A | 1/1990 | Zelmer et al. | |
| 4,969,912 A | 11/1990 | Kelman et al. | |
| 4,994,058 A | 2/1991 | Raven et al. | |
| 5,019,074 A | 5/1991 | Muller | |
| 5,171,318 A | 12/1992 | Gibson et al. | |
| 5,281,211 A | 1/1994 | Parel et al. | |
| 5,332,802 A | 7/1994 | Kelman et al. | |
| 5,461,212 A | 10/1995 | Seiler et al. | |
| 5,490,849 A | 2/1996 | Smith | |
| 5,512,966 A | 4/1996 | Snook | |
| 5,562,656 A | 10/1996 | Sumiya | |
| 5,599,340 A * | 2/1997 | Simon .................. A61F 9/00804 606/4 | |
| 5,624,437 A | 4/1997 | Freeman et al. | |
| 5,779,696 A | 7/1998 | Berry et al. | |
| 5,786,893 A | 7/1998 | Fink et al. | |
| 5,891,131 A | 4/1999 | Rajan et al. | |
| 5,910,110 A | 6/1999 | Bastable | |
| 6,033,396 A | 3/2000 | Huang et al. | |
| 6,139,876 A | 10/2000 | Kolta | |
| 6,161,544 A | 12/2000 | DeVore et al. | |
| 6,188,500 B1 | 2/2001 | Rudeen et al. | |
| 6,218,360 B1 | 4/2001 | Cintron et al. | |
| 6,270,221 B1 | 8/2001 | Liang et al. | |
| 6,280,436 B1 | 8/2001 | Freeman et al. | |
| 6,319,273 B1 | 11/2001 | Chen et al. | |
| 6,322,557 B1 | 11/2001 | Nikolaevich et al. | |
| 6,325,792 B1 | 12/2001 | Swinger et al. | |
| 6,394,999 B1 | 5/2002 | Williams et al. | |
| 6,478,792 B1 | 11/2002 | Hansel | |
| 6,520,956 B1 | 2/2003 | Huang | |
| 6,520,958 B1 | 2/2003 | Shimmick et al. | |
| 6,537,545 B1 | 3/2003 | Karageozian et al. | |
| 6,571,118 B1 | 5/2003 | Utzinger et al. | |
| 6,617,963 B1 | 9/2003 | Watters et al. | |
| 6,946,440 B1 | 9/2005 | DeWoolfson et al. | |
| 7,001,374 B2 | 2/2006 | Peyman | |
| 7,004,902 B2 | 2/2006 | Luce | |
| 7,044,945 B2 | 5/2006 | Sand | |
| 7,073,510 B2 | 7/2006 | Redmond et al. | |
| 7,331,350 B2 | 2/2008 | Kochevar et al. | |
| 7,402,562 B2 | 7/2008 | DeWoolfson et al. | |
| 7,731,362 B2 | 6/2010 | Gerlach | |
| 7,753,943 B2 | 7/2010 | Strong | |
| 7,898,656 B2 | 3/2011 | Yun et al. | |
| 7,935,058 B2 | 5/2011 | Dupps et al. | |
| 8,111,394 B1 | 2/2012 | Borysow et al. | |
| 8,115,919 B2 | 2/2012 | Yun et al. | |
| 8,366,689 B2 | 2/2013 | Marshall et al. | |
| 8,414,911 B2 | 4/2013 | Mattson et al. | |
| 8,475,437 B2 | 7/2013 | Mrochen et al. | |
| 2001/0055095 A1 | 12/2001 | D'Souza et al. | |
| 2002/0013577 A1 | 1/2002 | Frey et al. | |
| 2002/0159618 A1 | 10/2002 | Freeman et al. | |
| 2002/0164379 A1 | 11/2002 | Nishihara et al. | |
| 2003/0175259 A1 | 9/2003 | Karageozian et al. | |
| 2003/0189689 A1 | 10/2003 | Rathjen | |
| 2003/0231285 A1 | 12/2003 | Ferguson | |
| 2004/0002694 A1 | 1/2004 | Pawlowski et al. | |
| 2004/0093046 A1 | 5/2004 | Sand | |
| 2004/0199079 A1 | 10/2004 | Chuck et al. | |
| 2005/0038471 A1 | 2/2005 | Chan et al. | |
| 2005/0080467 A1 * | 4/2005 | Abe ................ A61F 9/00821 607/89 | |
| 2005/0096515 A1 | 5/2005 | Geng | |
| 2005/0149006 A1 | 7/2005 | Peyman | |
| 2005/0271590 A1 | 12/2005 | Schwartz et al. | |
| 2006/0135957 A1 | 6/2006 | Panescu | |
| 2006/0149343 A1 | 7/2006 | Altshuler et al. | |
| 2006/0195076 A1 | 8/2006 | Blumenkranz et al. | |
| 2006/0276777 A1 | 12/2006 | Coroneo | |
| 2007/0024860 A1 | 2/2007 | Tobiason et al. | |
| 2007/0048340 A1 | 3/2007 | Bran et al. | |
| 2007/0123845 A1 | 5/2007 | Lubatschowski | |
| 2007/0135805 A1 | 6/2007 | Peyman | |
| 2007/0142828 A1 | 6/2007 | Peyman | |
| 2007/0265603 A1 | 11/2007 | Pinelli | |
| 2008/0009901 A1 | 1/2008 | Redmond et al. | |
| 2008/0015660 A1 | 1/2008 | Herekar | |
| 2008/0063627 A1 | 3/2008 | Stucke et al. | |
| 2008/0114283 A1 | 5/2008 | Mattson et al. | |
| 2008/0139671 A1 | 6/2008 | Herekar | |
| 2008/0208177 A1 | 8/2008 | Mrochen et al. | |
| 2009/0116096 A1 | 5/2009 | Zalevsky et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0234335 A1 | 9/2009 | Yee | |
| 2009/0275929 A1 | 11/2009 | Zickler | |
| 2010/0028407 A1 | 2/2010 | Del Priore et al. | |
| 2010/0057060 A1 | 3/2010 | Herekar | |
| 2010/0069894 A1 | 3/2010 | Mrochen et al. | |
| 2010/0082018 A1 | 4/2010 | Panthakey et al. | |
| 2010/0094197 A1 | 4/2010 | Marshall et al. | |
| 2010/0114109 A1 | 5/2010 | Peyman | |
| 2010/0149487 A1 | 6/2010 | Ribak | |
| 2010/0173019 A1 | 7/2010 | Paik et al. | |
| 2010/0189817 A1 | 7/2010 | Krueger et al. | |
| 2010/0204584 A1 | 8/2010 | Ornberg et al. | |
| 2010/0210996 A1 | 8/2010 | Peyman | |
| 2010/0318017 A1 | 12/2010 | Lewis et al. | |
| 2011/0077624 A1 | 3/2011 | Brady et al. | |
| 2011/0098790 A1 | 4/2011 | Daxer | |
| 2011/0118654 A1 | 5/2011 | Muller et al. | |
| 2011/0152219 A1 | 6/2011 | Stagni et al. | |
| 2011/0190742 A1 | 8/2011 | Anisimov | |
| 2011/0202114 A1 | 8/2011 | Kessel et al. | |
| 2011/0208300 A1 | 8/2011 | Eugene et al. | |
| 2011/0237999 A1 | 9/2011 | Muller et al. | |
| 2011/0264082 A1 | 10/2011 | Mrochen | |
| 2011/0288466 A1 | 11/2011 | Muller et al. | |
| 2011/0301524 A1 | 12/2011 | Bueler et al. | |
| 2012/0065572 A1 * | 3/2012 | Lewis .................. G02C 7/047 604/20 | |
| 2012/0083772 A1 | 4/2012 | Rubinfield et al. | |
| 2012/0203161 A1 | 8/2012 | Herekar | |
| 2012/0215155 A1 * | 8/2012 | Muller .................. A61F 9/0079 604/20 | |
| 2012/0289886 A1 | 11/2012 | Muller et al. | |
| 2012/0302862 A1 | 11/2012 | Yun et al. | |
| 2012/0303008 A1 | 11/2012 | Muller et al. | |
| 2012/0310083 A1 | 12/2012 | Friedman et al. | |
| 2012/0310223 A1 | 12/2012 | Knox et al. | |
| 2013/0060187 A1 | 3/2013 | Friedman et al. | |
| 2013/0085370 A1 | 4/2013 | Friedman et al. | |
| 2013/0116757 A1 | 5/2013 | Russmann | |
| 2014/0194957 A1 | 7/2014 | Rubinfield et al. | |
| 2014/0249509 A1 | 9/2014 | Rubinfield et al. | |
| 2016/0310319 A1 * | 10/2016 | Friedman ................ A61F 9/008 | |

FOREIGN PATENT DOCUMENTS

| | | |
|---|---|---|
| EP | 1790383 | 5/2007 |
| IT | MI2010A001236 | 5/2010 |
| KG | 1376 | 8/2011 |
| RU | 2086215 | 8/1997 |
| RU | 2420330 | 6/2011 |
| RU | 2456971 | 7/2012 |
| WO | 2000074648 | 12/2000 |
| WO | 2001058495 | 8/2001 |
| WO | 2005110397 | 11/2005 |
| WO | 2006012947 | 2/2006 |
| WO | 2006128038 | 11/2006 |
| WO | 2007001926 | 1/2007 |
| WO | 2007053826 | 5/2007 |
| WO | 2007120457 | 10/2007 |
| WO | 2007139927 | 12/2007 |
| WO | 2007143111 | 12/2007 |
| WO | 2008000478 | 1/2008 |
| WO | 2008052081 | 5/2008 |
| WO | 2008095075 | 8/2008 |
| WO | 2009073213 | 6/2009 |

(56) References Cited

FOREIGN PATENT DOCUMENTS

| WO | 2009114513 | 9/2009 |
|---|---|---|
| WO | 2009146151 | 12/2009 |
| WO | 2010011119 | 1/2010 |
| WO | 2010015255 | 2/2010 |
| WO | 2010023705 | 3/2010 |
| WO | 2010093908 | 8/2010 |
| WO | 2011019940 | 2/2011 |
| WO | 2011116306 | 9/2011 |
| WO | 2012004726 | 1/2012 |
| WO | 2012149570 | 11/2012 |
| WO | 2012174453 | 12/2012 |
| WO | 2013148713 | 10/2013 |
| WO | 2013148895 | 10/2013 |
| WO | 2013148896 | 10/2013 |
| WO | 2013149075 | 10/2013 |
| WO | 2014202736 | 12/2014 |

OTHER PUBLICATIONS

Averianova, O. S., "Nastoyaschee I buduschee kross-linkage." Mir Ofalmologii, 2010, [online] [retrieved on Feb. 13, 2014] Retrieved from the internet: http:/ /miroft.org.ualpublications/.html.

Baier J. et al., "Singlet Oxygen Generation by UVA Light Exposure of Endogenous Photosensitizers," Biophysical Journal, vol. 91(4), pp. 1452-1459; Aug. 15, 2006 (8 pages).

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).

Barbarino, S. et al., "Post-LASIK ectasia: Stabilization and Effective Managmeent with Riboflavin / ultraviolet A-induced collagen cross-linking," Association for Research in Vision and Ophthalmology, 2006 (1 page).

Bruel, A., "Changes in Biomechanical Properties, Composition of Collagen and Elastin, and Advanced Glycation Endproducts of the Rat Aorta in Relation to Age," Atherosclerosis 127, Mar. 14, 1996 (11 pages).

Chace, K.V. et al., Abstract for "The role of nonenzymatic glycosylation, transition metals, and free radicals in the formation of collagen aggregates", Arch Biochem Biophys., Aug. 1, 1991, 288(2) pp. 473-480 (1 page).

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).

Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008 (10 pages).

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Coskenseven E. et al., "Comparative Study of Corneal Collagen Cross-linking With Riboflaving and UVA Irradiation in Patients With Keratoconus," Journal of Refractive Surgery, vol. 25, issue 4, pp. 371-376; Apr. 2009 (6 pages).

Erskine H., "Avedro Becomes Sponsor of US FDA Clinical Trials of Corneal Collagen Crosslinking," Press Release, Mar. 16, 2010 (1 page).

Fite et al. Noninvasive Multimodal Evaluation of Bioengineered Cartilage Constructs Combining Time-Resolved Fluorescence and Ultrasound Imaging Tissue Eng: Part C vol. 17, No. 4, 2011 (10 pages).

Friedman, M. et al. "Advanced Corneal Cross-Linking System with Fluorescence Dosimetry", Journal of Ophthalmology, vol. 2012, Article ID 303459, dated May 7, 2012 (6 pages).

Gibson, Q. et al., "The Oxidation of Reduced Flavin Mononucleotide by Molecular Oxygen," Biochem. J. (1962) 83, 368-377 (10 pages).

Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).

Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009 (11 pages).

Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009 (4 pages).

Hitzenberger et al., "Birefringence Properties of the Human Cornea Measured With Polarization Sensitive Optical Coherence Tomography," Bull. Soc. Beige Ophtalmol., 302, 153-168, 2006.

Holmstrom, B. et al., "Riboflavin as an Electron Donor in Photochemical Reactions," 1867-1871, Nov. 29, 1960 (5 pages).

IMEX, "KXL System: Crosslinking Para Cirugia Corneal Bibliografia Cientifica," Product Literature, Nov. 23, 2010 (24 pages).

Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).

Kampik D. et al., "Influence of Corneal Collagen Crosslinking With Riboflavin and Ultraviolet-A Irradiation on Excimer Laser Surgery," Investigative Opthalmology & Visual Science, vol. 51, No. 8, pp. 3929-3934; Aug. 2010 (6 pages).

Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.

Kanellopoulos, A. J., "Keratoconus management: UV A-induced collagen cross-linking followed by a limited topo-guided surface excimer ablation," American Academy of Ophthalmology, 2006 (25 pages).

Kanellopoulos, A. J., "Ultraviolet a cornea collagen cross-linking, as a pre-treatment for surface excimer ablation in the management of keratoconus and post-LASIK ectasia," American Academy of Ophthalmology, 2005 (28 pages).

Kissner Anja, et al., "Pharmacological Modification of the Epithelial Permeability by Benzalkonium Chloride in UVNRiboflavin Corneal Collagen Cross-Linking," Current Eye Research 35(8), pp. 715-721; Mar. 2010 (7 pages).

Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, val. 224, No. 9, pp. 700-706; Sep. 2007 (7 pages).

Koller, T. et al., "Complication and failure rates after corneal crosslinking," Journal Cataract and refractive surgery, vol. 35, No. 8, Aug. 2009, pp. 1358-1362.

Kornilovsky, I. M. "Novye neinvazivnye tekhnologii lazernoy modifikatsii optiko-refraksionnykk struktur glaza. Refraktsionnaya khirurgiya I oftalmologiya" vol. 9, No. 3, 2006 (pts. 17-26).

Krueger Ronald R., "Rapid VS Standard Collagen CXL with Equivalent Energy Dosing," presentation slides, (26 pages); available at http://www.slideshare.net/logen/krueger-kerekar-rapid-cross-linking (date unknown, prior to Nov. 9, 2009).

Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).

Li, C. et al. "Noncontact All-Optical Measurement of Corneal Elasticity." Optics Letters. vol. 37, No. 10, May 15, 2012 (pp. 1625-1627).

Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).

Marzouky, et. al., Tensioactive-mediated Transepithelial Corneal Cross-linking—First Laboratory Report, European Ophthalmic Review, 2009, 3(2), pp. 67-70.

Massey, V., "Activation of Molecular Oxygen by Flavins and Flavoproteins," The Journal of Biological Chemistry vol. 269, No. 36, Issue of Sep. 9, pp. 22459-22462, 1994 (4 pages).

(56) References Cited

OTHER PUBLICATIONS

Meek, K.M. et al. "The Cornea and Sclera", Collagen: Structure and Mechanics, Chapter 13, pp. 359-396, 2008 (38 pages).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
Pinelli R., et al., "C3-Riboflaving Treatments: Where Did We Come From? Where Are We Now?" Cataract & Refractive Surgery Today Europe, Summer 2007, pp. 36-46; Jun. 2007 (10 pages).
Pinelli, R. "Corneal Cross-Linking with Riboflavin: Entering a New Era in Ophthalmology." Ophthalmology Times Europe. vol. 2, No. 7, Sep. 1, 2006 (3 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurement and Intrepretation of Brillouin Scattering in the Lens of the Eye," The Royal Society, Abstract only, published 2013 [available online at http://rspb.royalsocietypublishing.org/content/214/11971449.short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).
Rocha K., et al., "Comparative Study of Riboflavin-UVA Crosslinking and "Flash-linking" Using Surface Wave Elastometry," Journal of Refractive Surgery, vol. 24 Issue 7, pp. S748-S751; Sep. 2008 (4 pages).
Rolandi et al. Correlation of Collagen-Linked Fluorescence and Tendon Fiber Breaking Time. Gerontology 1991;27 :240-243 (4 pages).
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Spoerl E. et al., "Safety of UVA-Riboflavin Cross-Linking of the Cornea," Cornea, vol. 26, No. 4, pp. 385-389; May 2007 (5 pages).
Spoerl E., et al., "Artificial Stiffening of the Cornea by Induction of Intrastromal Cross-links," Oer Ophthalmologe, vol. 94, No. 12, pp. 902-906; Dec. 1997 (5 pages).
Spoerl E., et al., "Induction of Cross-links in Corneal Tissue," Experimental Eye Research, vol. 66, Issue 1, pp. 97-103; Jan. 1998 (7 pages).
Spoerl E., et al., "Techniques for Stiffening the Cornea," Journal of Refractive Surgery, vol. 15, Issue 6, pp. 711-713; Nov.-Dec. 1999 (4 pages).
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thorton, I. et al., "Biomechancial Effects of Intraocular Pressure Elevation on Optic Berve/Lamina Cribrosa before and after Peripapillary Scleral Collagen Cross-Linking." Invest. Ophthalmol. Vis. Sci., Mar. 2009, 50(3): pp. 1227-1233.
UV-X: Radiation System for Treatment of Keratokonus, PESCHKE Meditrade GmbH; retrieved from http://www.peschkemed.ch/ on Sep. 27, 2011 (1 page) (date unknown, prior to Sep. 16, 2008).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Sliffiless of the Collagen Network in Human Articular Cartilage Arthritis & Rheumatism vol. 46, No. 1, Jan. 2002, pp. 114-123 (10 pages).
Wollensak G., "Crosslinking Treatment of Progressive Keratoconus: New Hope," Current Opinion in Ophthalmology, vol. 17(4), pp. 356-360; Aug. 2006 (5 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).
Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Wong, J. et al., "Post-Lasik ectasia: PRK following previous stablization and effective management with Riboflavin I ultraviolet A-induced collagen cross-linking," Association for Research in Vision and Ophthalmology, 2006 (1 page).
Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970).
Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 5, 2011 (pp. 13011-13022).
International Patent No. PCT/US2020/045299, International Search Report, dated Oct. 22, 2020, 2 pages.
International Patent No. PCT/US2020/045299, Written Opinion of the ISR, dated Oct. 22, 2020, 4 pages.

* cited by examiner

| Inputs | | | | Outputs | | | | | | |
|---|---|---|---|---|---|---|---|---|---|---|
| | $D_{spot}$, μm | Pitch, μm | Visits | Spots | Shoots | Visit time, s | Shoot time, ms | Peak irrad., W/cm² | Laser power, mW | Peak dose per shoot, J/cm² | Nonuniformity, % |
| A | 40 | 38.1 | 10 | 9997 | 99970 | 100 | 9.8 | 105.48 | 1.91 | 1.03 | 4.775 |
| B | 100 | 95.2 | 50 | 1615 | 80750 | 20 | 12.2 | 16.97 | 1.92 | 0.207 | 4.775 |
| C | 150 | 142.85 | 120 | 721 | 86520 | 8.33 | 11.36 | 7.59 | 1.93 | 0.086 | 4.775 |
| D | 200 | 190.5 | 220 | 397 | 87340 | 4.55 | 11.25 | 4.18 | 1.89 | 0.047 | 4.773 |
| E | 250 | 238.1 | 350 | 253 | 88550 | 2.86 | 11.1 | 2.66 | 1.885 | 0.0295 | 4.773 |

PHOTOACTIVATION SYSTEMS AND METHODS FOR CORNEAL CROSS-LINKING TREATMENTS

CROSS-REFERENCE TO RELATED APPLICATIONS

This application claims priority to, and the benefit of, U.S. Provisional Patent Application Ser. No. 62/883,197, filed Aug. 6, 2019, the contents of which are incorporated entirely herein by reference.

BACKGROUND

Field

The present disclosure pertains to systems and methods for eye treatments, and more particularly, to systems and methods for photoactivating a cross-linking agent.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

Cross-linking treatments may also be employed to induce refractive changes in the cornea to correct disorders such as myopia, hyperopia, astigmatism, irregular astigmatism, presbyopia, etc.

SUMMARY

Embodiments include systems and methods for photoactivating a cross-linking agent in corneal cross-linking treatments. Using a laser light source to achieve a scanned light pattern can provide advantages for photoactivating a cross-linking agent. In particular, scanning parameters for the laser can be optimized to increase the efficacy of individual treatments. For instance, treatment time, total dose, intensity/irradiance of the laser beam, pulsing of the laser beam, size of the spot defined by the laser beam (laser spot size), velocity or duration of application of the laser spot, and/or frequency of repetition of portions of the scan pattern can be controlled to enhance cross-linking activity. Such parameters can be optimized according to the photochemical kinetic reactions involved in cross-linking activity as described above. These reactions determine the consumption and replenishment of oxygen during cross-linking activity, supply and photo-degradation of the cross-linking agent molecules, and depth of effect.

According to an example embodiment, a system for treating an eye includes a laser light source configured to provide photoactivating light. The system includes a scanning system configured to receive the photoactivating light as a laser beam and to move the laser beam over a cornea treated with a cross-linking agent. The system includes a controller configured to provide control signals to programmatically control the laser light source and the scanning system. The one or more control signals causing the laser beam to visit one or more regions of the cornea more than once according to a scan pattern and expose the one or more regions to the photoactivating light. The photoactivating light causes the cross-linking agent in the one or more exposed regions to react with oxygen to generate cross-linking activity in the one or more exposed regions. The scan pattern causes a predetermined period of time to pass between visits by the laser beam to the one or more exposed regions, the predetermined period of time allowing oxygen in the one or more exposed regions to replenish and allow a desired amount of the cross-linking activity to be generated with sufficient oxygen during each visit to the one or more exposed regions.

According to another example embodiment, a method for treating an eye includes generating photoactivating light with a laser light source. The method includes directing the photoactivating light as a laser beam to a scanning system. The method includes operating the scanning system to cause the laser beam to move over the cornea and visit one or more regions of the cornea more than once according to a scan pattern and expose the one or more regions to the photoactivating light. The photoactivating light causes the cross-linking agent in the one or more exposed regions to react with oxygen to generate cross-linking activity in the one or more exposed regions. The method includes optimizing the scan pattern to cause a predetermined period of time to pass between visits by the laser beam to the one or more exposed regions, the predetermined period of time allowing oxygen in the one or more exposed regions to replenish and allow a desired amount of the cross-linking activity to be generated with sufficient oxygen during each visit to the one or more exposed regions.

BRIEF DESCRIPTION OF THE DRAWINGS

FIG. 11 illustrates different example combinations of parameter values for laser scanning applying discrete dots according to a grid inside a boundary defining a treatment zone, according to aspects of the present disclosure.

Figure 1:
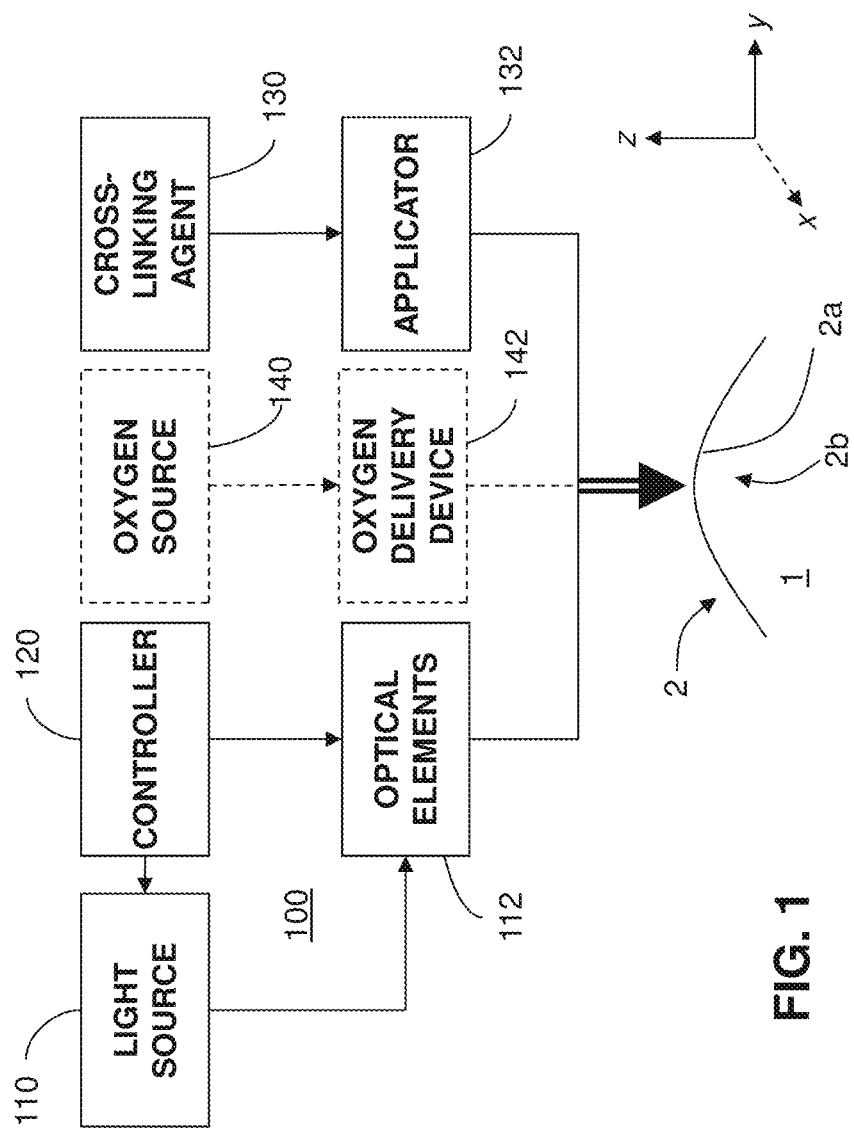
FIG. 1 illustrates an example system that delivers a cross-linking agent and photoactivating light to a cornea of an eye in order to generate cross-linking of corneal collagen, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent are described in U.S. Patent Application Publication No. 2017/0296383, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b (also known as an "epi-on" procedure). Alternatively, the corneal epithelium 2a may be removed or otherwise incised to allow the cross-linking agent 130 to be applied more directly to the underlying tissue (also known as an "epi-off" procedure).

The treatment system 100 includes an illumination system with a light source 110 and optical elements 112 for directing light to the cornea 2. In some embodiments, the light source 110 may include a light emitting diode (LED). In other embodiments, the light source 110 may provide a laser. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm or 375 nm, or a wavelength falling within the band of 315 nm to 400 nm) light. Alternatively, the photoactivating light may include another wavelength, such as a visible wavelength (e.g., approximately 452 nm) or any other wavelength selected to activate a photosensitizing agent. As described further below, corneal cross-linking improves corneal strength by creating chemical bonds within the corneal tissue according to a system of photochemical kinetic reactions.

Riboflavin and the photoactivating light may be applied to stabilize and/or strengthen corneal tissue to address corneal ectatic disorders, such as keratoconus or post-LASIK ectasia. The application of riboflavin and the photoactivating light may also allow for various amounts of refractive correction, which for instance, may involve combinations of myopia, hyperopia, astigmatism, irregular astigmatism, presbyopia and complex corneal refractive surface corrections due to corneal ectatic disorders as well as other conditions of corneal biomechanical alteration/degeneration, etc.

The treatment system 100 includes one or more controllers 120 that control aspects of the treatment system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors, lenses, or other optical components for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more optical sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

According to some aspects, optical elements of an example treatment system may employ fiber-optic elements. The use of fiber-optic elements can eliminate the need for free space optical elements as well as opto-mechanical mounts in a treatment system. Advantageously, the use of fiber-optics can reduce the size and footprint of a treatment system, reduce design and manufacturing complexity and cost, and enhance reliability.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a microelectromechanical system (MEMS) device, e.g., a digital micro-mirror device (DMD), to modulate the application of photoactivating light spatially and temporally. Using DMD technology, the photoactivating light from the light source 110, e.g., an LED, is projected in a precise spatial pattern that is created by microscopically small mirrors laid out in an array on a semiconductor chip. Each mirror represents one or more pixels in the pattern of projected light. With the DMD one can perform topography guided cross-linking. The control of the DMD according to topography may employ several different spatial and temporal irradiance and dose profiles. As described further below, these spatial and temporal dose profiles may be created using continuous wave (CW) illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real time monitoring and modulation of corneal cross-linking during treatment. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking. The UVA light may be applied continuously (CW) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness imparted based on the modulated frequency, duty cycle, irradiance and dose delivered to the cornea, complex biomechanical stiffness patterns may be imparted to the cornea. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference. Embodiments may generate cross-linking activity in the cornea according to circular and/or annular patterns defined by the delivery of photoactivating light (e.g., via the DMD described above). Additionally or alternatively, embodiments may generate cross-linking activity in the cornea according to non-circular and/or non-annular patterns defined by the delivery of photoactivating light (e.g., via the DMD).

Patterns of photoactivating light can be applied (e.g., via the DMD) to the eye in separate treatment zones with different doses sequentially or continuously applied. For instance, one treatment zone can be "turned off" (i.e., delivery of the corresponding photoactivating light ceases) while another "stays on" (i.e., delivery of the corresponding photoactivating light continues). The treatment zones can be, for instance, annularly shaped about a center point of the eye. There may also be discontinuous zones where no the photoactivating light is applied (e.g., a central treatment zone surrounded by an annulus of no light surrounded by an annular treatment zone of light, etc.). The widths of the annular zones can be of different dimensions, e.g., one annular zone has a width of 1 mm and another has a width of 2 mm. Applying the photoactivating light in annular treatment zones on the periphery of the eye without a central treatment zone can result in a hyperopic correction, for instance, by causing the central region of the eye to have an increased curvature while the periphery is strengthened. In some cases, central and surrounding treatment zones can be elliptical in shape, for instance to address astigmatism, by preferentially generating cross-linking activity in regions of the cornea to correct the astigmatism. Such elliptically shaped annular treatment zones are preferentially oriented with the axis of the annular treatment zones aligned according to the orientation of the astigmatism. The elliptically shaped treatment zones can also be irregularly asymmetric (i.e., having major and minor axis that are not perpendicular and can be situated with distinct center points (centers of mass)).

Cross-linking treatments can be tuned according to one or more biomechanical properties of the eye, such as the corneal topography (i.e., shape), corneal strength (i.e., stiffness), and/or corneal thickness. Optical correction and/or strengthening of the cornea can be achieved by applying the cross-linking agent and/or photoactivating light in one or more iterations with adjustable characteristics for each iteration. Generally, a developed treatment plan can include a number of applications of the cross-linking agent, the amount and concentration of the cross-linking agent for each application, the number of applications of photoactivating light, and the timing, duration, power, energy dosage, and pattern of the photoactivating light for each application. Furthermore, the cross-linking treatments can be adapted based on feedback information relating to the biomechanical properties gathered in real time during treatment or during breaks in treatments.

When riboflavin absorbs radiant energy, especially light, it undergoes photoactivation. There are two photochemical kinetic pathways for riboflavin photoactivation, Type I and Type II. The reactions involved in both the Type I and Type II mechanisms and other aspects of the photochemical kinetic reactions generating cross-linking activity are described in U.S. Pat. No. 10,350,111, filed Apr. 27, 2016 and titled "Systems and Methods for Cross-Linking Treatments of an Eye," the contents of which are incorporated entirely herein by reference.

Corneal cross-linking reactions are rate limited by oxygen concentrations in the corneal tissue. Thus, the addition of oxygen also affects the amount of corneal cross-linking. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

As described above, the treatment system 100 includes optical elements 112 that direct light (e.g., UV light) from a light source 110 to photoactivate the cross-linking agent 130 (e.g., riboflavin) applied to the cornea 2 and thus generate cross-linking activity. In particular, the photoactivating light can be selectively directed to regions of the cornea 2 according to a particular spatial treatment pattern. In some embodiments, a treatment system can provide an adjustable treatment pattern so that different ophthalmic conditions can be treated with the same treatment system.

Example treatment systems that treat different ophthalmic conditions by providing different treatment patterns are described in U.S. Patent Application Publication No. 2020/0107953, filed Oct. 9, 2019 and titled "Photoactivation Systems and Methods for Corneal Cross-Linking Treatments," the contents of these application being incorporated entirely herein by reference.

Scanning Treatment Systems

Figure 2A:
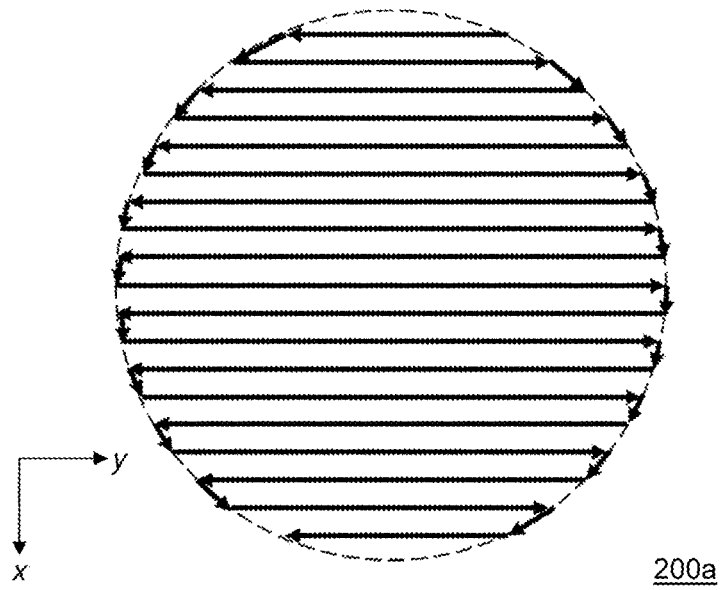
FIG. 2A illustrates an example circular treatment pattern that can be produced with a XY scanning mirror pair.
Figure 2B:
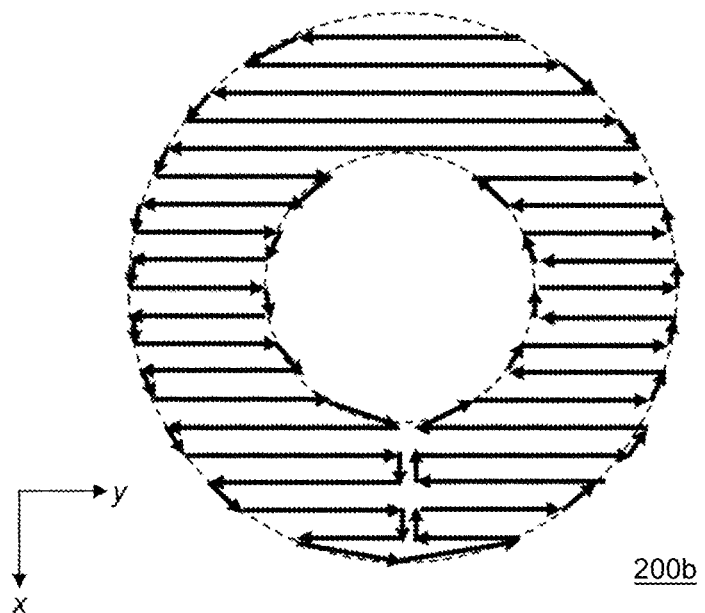
FIG. 2B illustrates an example annular treatment pattern that that can also be produced with a XY scanning mirror pair.

Optical elements of an example treatment system include a XY scanning mirror pair (e.g., instead of a DMD) that can scan a UV light beam to form a UV light pattern with a small, high-quality spot. (The depth of the cornea is measured along a z-axis and patterns of photoactivating light may be projected on transverse x-y planes.) For instance, FIG. 2A illustrates an example circular treatment pattern 200a that can be produced with a XY scanning mirror pair. FIG. 2B illustrates an example annular treatment pattern 200b that that can also be produced with a XY scanning mirror pair.

Figure 3:
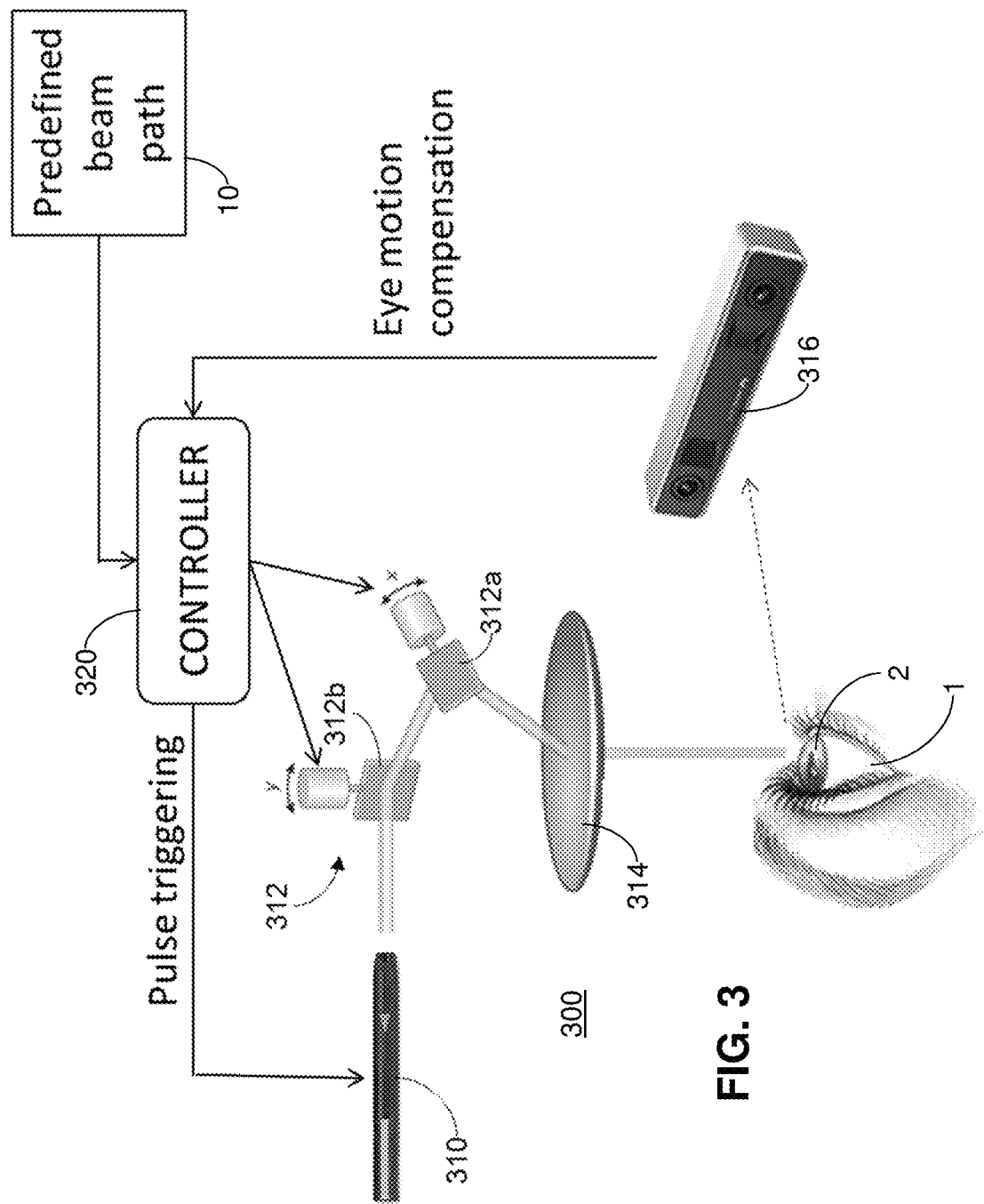
FIG. 3 illustrates an example treatment system that provides a laser-based approach for projecting patterns of photoactivating light to a cornea employing a XY scanning system, according to aspects of the present disclosure.

FIG. 3 illustrates an example scanning treatment system 300. The treatment system 300 includes a UV (e.g., UVA) laser source 310 and a galvanometer mirror system (or dual-axis MEMS mirror) 312 that acts as a XY scanning system. The laser source 310 may employ a xenon fluoride (XeF) excimer laser, femtosecond pulse laser, or a laser diode. The laser source 310 may be implemented with a light amplitude modulator (either internal or external to the laser source 310). The treatment system 300 includes a controller 320 that may control aspects of the treatment system 300. In particular, the controller 320 can trigger the laser source 310 to deliver a laser beam in pulses as described above.

The laser beam from the laser source 310 produces a small, high-quality spot on the galvanometer mirror system 312. The galvanometer mirror system 312 includes a X mirror 312a that can scan the UV light beam in the x-direction and a Y mirror 312b that can scan the UV light beam in the y-direction. The controller 320 can control the galvanometer mirror system 312 to scan the laser beam in the x- and y-directions according to a predefined scan pattern 10. The scan pattern 10 can be translated to cause the X mirror 312a and the Y mirror 312b to scan the laser beam in the x- and y-directions, respectively. In particular, the controller 320 can transmit a X position signal to the X mirror 312a to control a tilt angle of the X mirror 312a and direct the laser beam to a desired position along the x-axis. Correspondingly, controller 320 can transmit a Y position signal to the Y mirror 312b to control a tilt angle of the Y mirror 312b and direct the laser beam to a desired position along the y-axis. The treatment system 300 also includes a lens 314 (e.g., a telecentric, f-theta, or other scanning lens) that transmits the scanned laser beam to the cornea 2. Additionally or alternatively, a lens may be positioned between the laser 310 and the X mirror 312a. Light from the laser source 310 may be transmitted via free space or may be coupled to an optical fiber for transmission to the vicinity of the galvanometer mirror system 312 or lens 314. Fiberoptic transmission has the added benefit of allowing the laser source 310 to be positioned remotely from the other system elements, simplifying system design. The speed of the first mirror and/or second mirrors of the galvanometer mirror system 312 can be adjusted during part of the scan in order to increase or decrease dwell time over a portion of the scan pattern, thereby adjusting the corresponding dose of UV light applied in portions of the scan pattern.

The treatment system 300 also includes an eye tracking system. In particular, the treatment system 300 includes an eye position and orientation detecting system 316 (e.g., a camera that captures images of the eye 1). The controller 320 can receive and process the information (e.g., images) from the eye position detecting system 316 to determine the position of the cornea 2 relative to the treatment system 300. To compensate for changes in the position of the cornea 2, the controller 320 can control the galvanometer mirror system 312 to adjust the scanned laser beam and cause the scan pattern 10 to be applied to the desired areas of the cornea 2. As such, the detecting system 316 and the controller 320 combine to provide an eye tracking system.

In general, scanning treatment systems can apply photoactivating light according to a pattern to achieve a predefined treatment zone (e.g., circular, annular, or other shape) at the corneal surface. Aspects of a scan pattern may be defined by a continuous line. As shown with the example patterns 200a, 200b of FIGS. 2A-B, a continuous line may formed by scanning the laser in connected piecewise paths.

Figure 4:
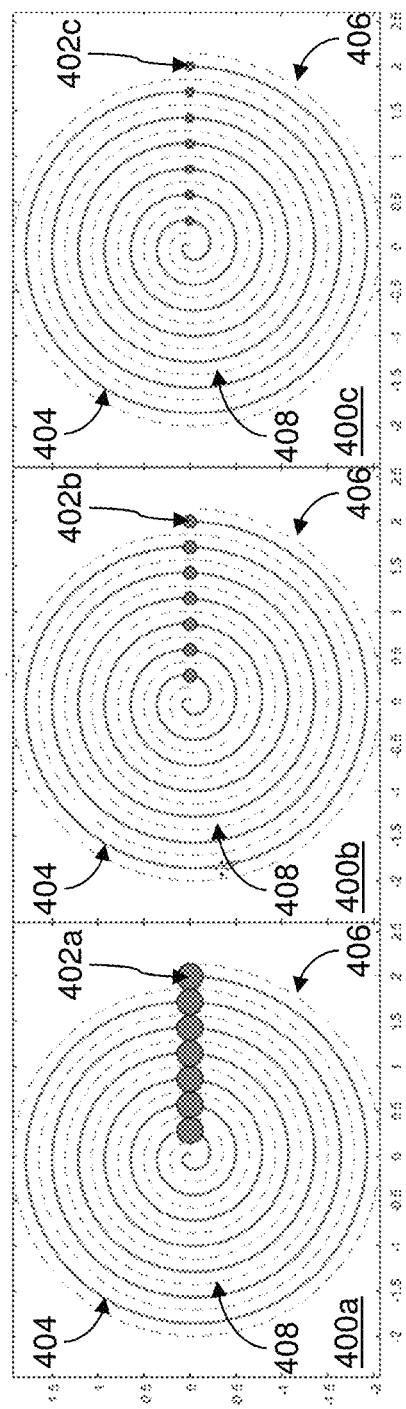
FIG. 4A illustrates an example treatment zone where a laser beam has a spot size with a diameter that is sufficiently large to apply photoactivating light in a spiral to 100% of an area defined by a substantially circular boundary, according to aspects of the present disclosure.
FIG. 4B illustrates another example treatment zone where a laser beam has a spot size with a diameter that is 50% of the diameter shown in FIG. 4A, according to aspects of the present disclosure.
FIG. 4C illustrates yet another example treatment zone where a laser beam has a spot size with a diameter that is 25% of the diameter shown in FIG. 4A, according to aspects of the present disclosure.

Alternatively, a continuous line may formed by scanning the laser without interruption. For instance, as shown in FIGS. 4A-C, a continuous line may formed by scanning the laser in a spiral 404 without interruption.

Additionally or alternatively, aspects of a scan pattern may be defined by a plurality of unconnected straight or curved lines. For instance, a scan pattern may include lines defined by a series of dashes.

Additionally or alternatively, aspects of a scan pattern may be defined by a plurality of discrete dots. For instance, a scan pattern may include lines defined by a series of discrete dots. In some embodiments, a sequence of discrete dots can be applied with an optical element, such as a diffractive element as described further below, to simultaneously form multiple laser spots which are individually scanned to define the treatment zone.

Various types of patterns of photoactivating light for cross-linking treatments are described herein. The choice of pattern may depend on different optimization criteria including, but not limited to, uniformity of photoactivating light dose over the treatment zone, desired maximum cross-linking efficiency, and maximum correction (e.g., refractive correction) for the eye. Furthermore, the choice of pattern may be constrained by considerations including, but not limited to, compliance to eye safety standards, predefined treatment time, predefined light dose, limits on scan velocity imposed by optical elements and other components of the treatment system, and laser power specifications.

Laser Scanning Optimization

Using a laser light source to achieve a scanned light pattern can provide benefits for corneal cross-linking treatments over approaches that employ a LED light source. In particular, scanning parameters for the laser can be optimized to increase the efficacy of individual treatments. For instance, treatment time, total dose, intensity/irradiance of the laser beam, pulsing of the laser beam, size of the spot defined by the laser beam (laser spot size), velocity or duration of application of the laser spot, and/or frequency of repetition of portions of the scan pattern can be controlled to enhance cross-linking activity. Such parameters can be optimized according to the photochemical kinetic reactions involved in cross-linking activity as described above. These reactions determine the consumption and replenishment of oxygen during cross-linking activity, supply and photodegradation of the cross-linking agent molecules, and depth of effect.

For instance, laser spot size can be optimized to achieve the desired treatment. FIGS. 4A-C also illustrate how different treatment zones can be achieved by varying the laser spot size. In particular, FIG. 4A illustrates an example treatment zone 400a where a beam from a laser source, e.g., the UV laser source 210 or the UV light source 310, forms a spot size with a diameter 402a that is sufficiently large to apply photoactivating light in a spiral 404 to 100% of an area 408 defined by a substantially circular boundary 406. Meanwhile, FIG. 4B illustrates an example treatment zone 400b where a beam from the laser source has a spot size with a diameter 402b that is 50% of the diameter shown in FIG. 4A. As such, as the beam in FIG. 4B travels over the same spiral 404, photoactivating light is applied to less of the area 408 defined by the substantially circular boundary 406. As shown in FIG. 4B, the diameter 402b is too small to allow the laser beam to cover the space between adjacent portions of the spiral 404. FIG. 4C illustrates yet another example treatment zone 400c where a beam from the laser source has a spot size with a diameter 402c that is 25% of the diameter 402a shown in FIG. 4A. As such, as the beam in FIG. 4C travels over the same spiral 404, photoactivating light is applied even less of the area 408 defined by the substantially circular boundary 406. Accordingly, varying the laser spot size can determine the areas of the cornea (treatment zone) that receive photoactivating light and experience cross-linking activity. Optimizing the size of the laser spot in relation to the pitch of the spiral pattern has the effect of increasing oxygen diffusion into the treated spots from the untreated spots, which is advantageous for maintaining an aerobic state in the treated spots and therefore increasing crosslinking efficiency.

Additionally or alternatively, frequency of repetition for portions of the scan pattern can be optimized to achieve the desired treatment. For instance, the laser beam may travel over portions of a given scan pattern more than once. Furthermore, the laser beam may be scanned over these portions in different sequences. For instance, a scan pattern may include portions A, B, and C. In an initial pass, the laser beam may travel over portion A, then portion B, and then portion C. During a subsequent pass, the laser beam may travel over portion C, then portion B second, and then portion A. The laser beam may also transform aspects of the scan pattern as it travels over portions of the given scan more than once. For instance, during a subsequent pass by the laser beam, the scan pattern or portions thereof may be rotated and/or shifted laterally relative to the first pass. Optimizing the frequency of repetition of the scan pattern has the effect of preventing depletion of oxygen within the treated spots, which is advantageous for maintaining an aerobic state in the treated spots and therefore increasing crosslinking efficiency.

Additionally or alternatively, characteristics of the laser beam delivered to the XY scanning system can be optimized to achieve desired treatment. For instance, the laser beam may be delivered according to particular pulsing parameters as described above. In some cases, a pulsed laser beam may be delivered to the XY scanning system while the XY scanning system travels continuously over selected portions of the scan pattern, so that a pattern of dashes is generated over those portions.

The intensity and/or duration of the laser beam delivered to the XY scanning system at different portions of the scan pattern can be optimized to provide desired doses of photoactivating light at desired areas of the treatment zone. For instance, the intensity of the laser beam may be modulated for selected portions of the scan pattern to apply different irradiances at different locations on the cornea. The laser beam may also be applied with particular durations and irradiance for selected portions of the scan pattern.

If a continuous scan pattern such as spiral pattern is applied, the pitch between spiral lines can additionally be optimized. If a discontinuous scan pattern such as a random, semi-random, or matrix-based pattern is applied, the dwell time on each spot, distance between spots, and travel time between spots can additionally be optimized.

Figure 5:
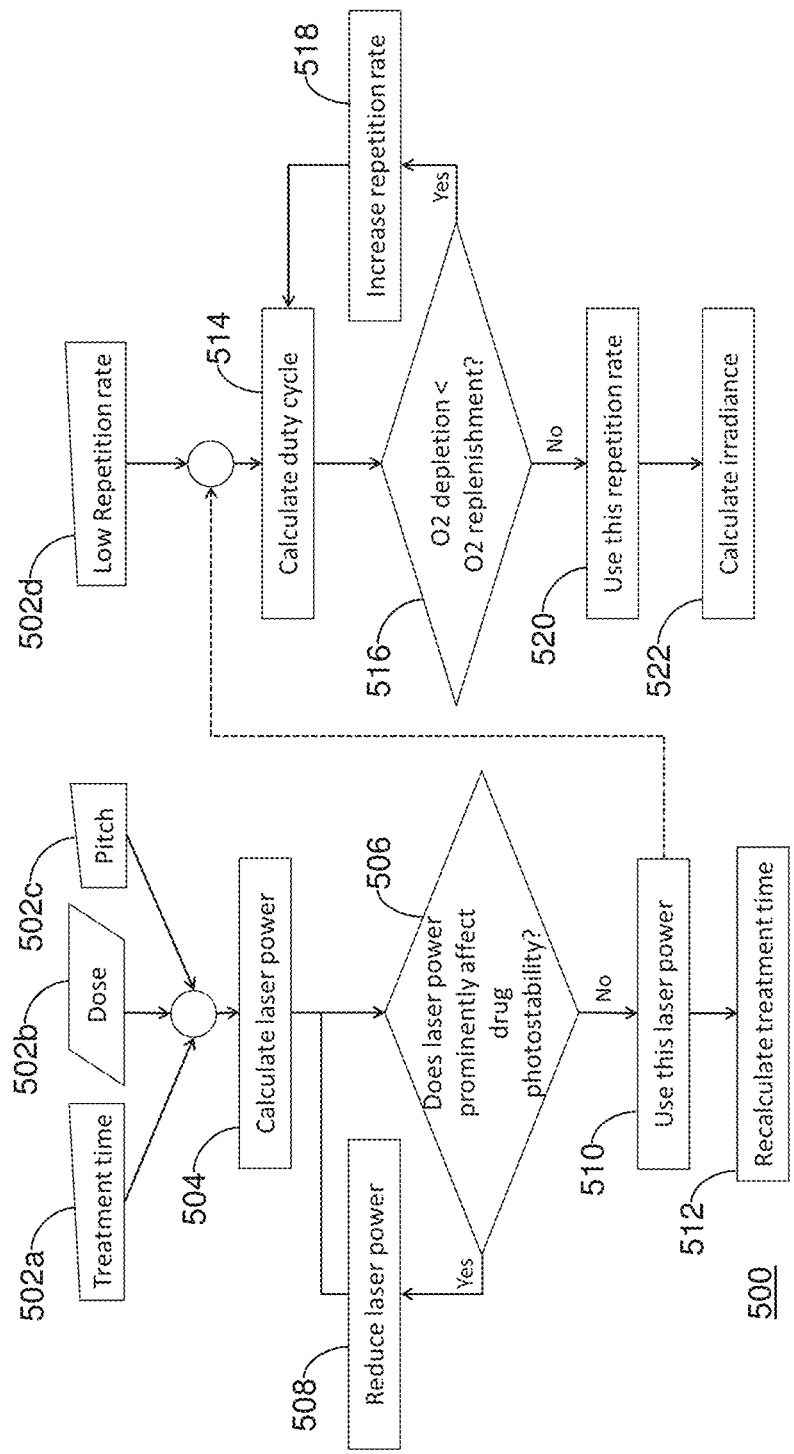
FIG. 5 illustrates a flowchart for an example process for optimizing laser scanning parameters for cross-linking treatments, according to aspects of the present disclosure.

FIG. 5 illustrates a flowchart for an example process 500 for optimizing laser scanning parameters for cross-linking treatments. An initial treatment time 502 a, a dose 502 b of photoactivating light, a pitch 502 c for the scan pattern, and an initial repetition rate 502 d are specified for the optimization process 500. In act 504, the optimization process 500 calculates a laser power based on the initial treatment time 502 a, the initial dose 502 b, and the pitch 502 c. In act 506, the optimization process 506 determines whether the calculated laser power affects the photostability of the cross-linking agent. If photostability is affected 508, the optimization process 500 returns to act 504 to recalculate the laser power until it determines, in act 506, that the photostability is not affected. In act 510, the optimization process 500 selects the laser power which does not affect photostability. In act 512, the optimization process 500 recalculates the treatment time based on the selected laser power. In act 514, the optimization process 500 calculates a duty cycle based on the initial repetition rate 502 d and the selected laser power. In act 516, the optimization process 500 compares oxygen depletion and oxygen replenishment with the calculated duty rate. If oxygen depletion is less than oxygen replenishment, the optimization process 500 increases the repetition rate in 518 and returns to act 514 where it recalculates the duty cycle based on the increased repetition rate. The optimization process 500 selects the duty cycle in act 520 once it determines that the oxygen depletion is not less than oxygen replenishment. In act 522, the optimization process 500 calculates an irradiance for the photoactivating light based on the selected duty cycle. The optimization process may conceptually be completed once or a discrete number of times, for example in a laboratory, in order to generate a preset list of optimized parameter combinations. Alternatively, the optimization process may be conducted on demand by software in response to user inputs in order to generate a specific parameter combination prior to treatment.

Certain scanning parameters may be related. For instance, if the total dose is kept constant, increasing the laser power decreases the treatment time, or vice versa. Experimental data indicates that longer treatment times and higher repetition rates usually result in a significant increase in flattening of the cornea, while the change in the laser power does not significantly affect flattening. (It is noted, however, extremely high laser powers, in addition raising safety concerns, can adversely affect flattening by degrading drug molecules to by-products that produce less efficient crosslinking.)

Figure 6:
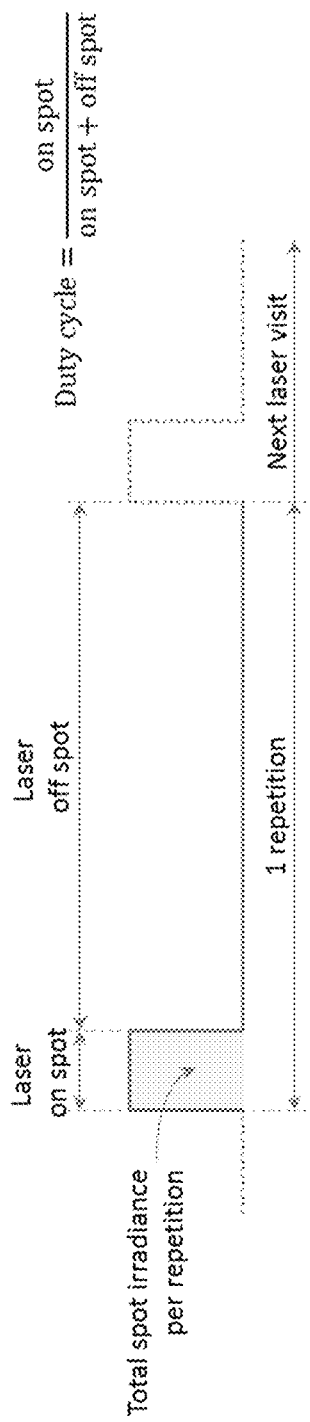
FIG. 6 illustrates an example repetition cycle for laser scanning in a cross-linking treatment, according to aspects of the present disclosure.

Experimental results indicate that increasing repetition rate, thus increasing the number of visits to the same location by the laser beam, can significantly enhance crosslinking activity. To achieve greater flattening, the repetition rate, or equivalently the number of visits, can be increased until the time for oxygen replenishment is on the order of the off-duty duration for each location. This allows sufficient time between two consecutive visits for the oxygen to replenish at each location. FIG. 6 illustrates an example repetition cycle 600 for a cross-linking treatment. During each visit, one location receives a specific amount of laser irradiance for photoactivation, followed by an off-cycle where the laser beam is delivered to other locations. The total irradiance per location per repetition depends on the scan velocity as well as the laser power. The number of laser visits per location is maximized while the off-duty duration is sufficient to allow oxygen replenishment. Preferably, the on-duty duration is shorter than the time needed for complete oxygen depletion.

Figure 7:
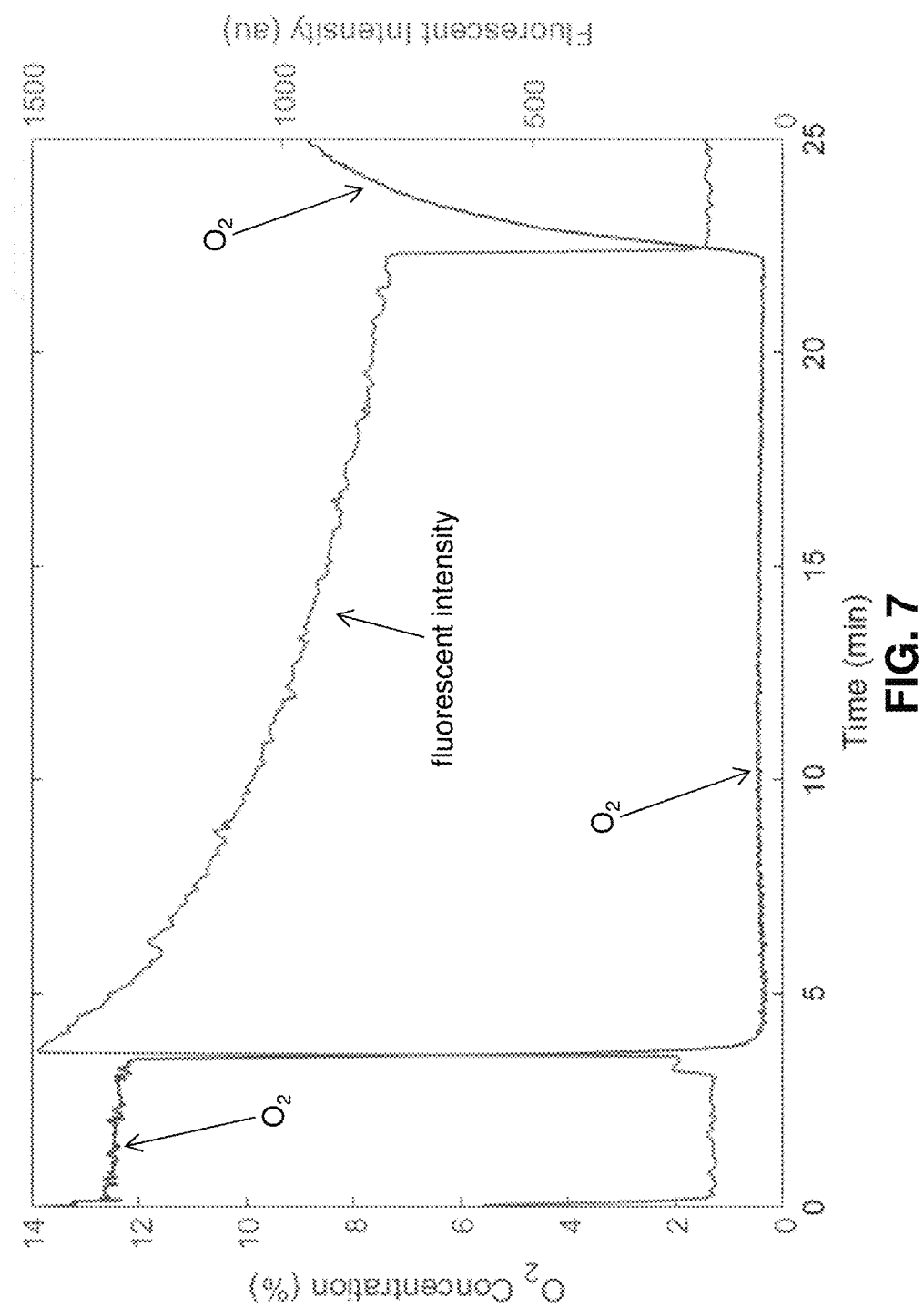
FIG. 7 illustrates oxygen concentration and fluorescent intensity associated with the cross-linking agent at a location during an example cross-linking treatment employing laser scanning, according to aspects of the present disclosure.
Figure 8A:
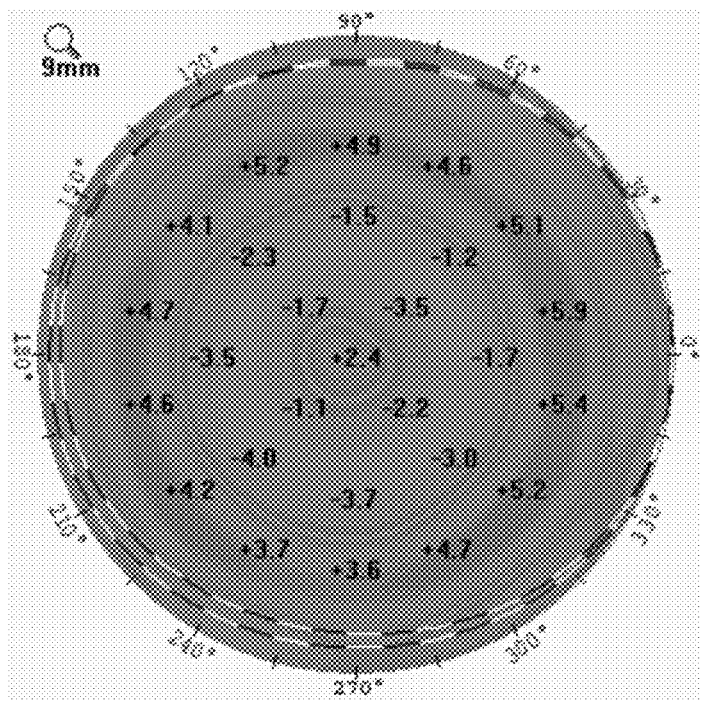
FIGS. 8A-E illustrate curvature change resulting from treatments of five eyes where the epithelium layer is left on the eye (epi-on), according to aspects of the present disclosure.
Figure 8B:
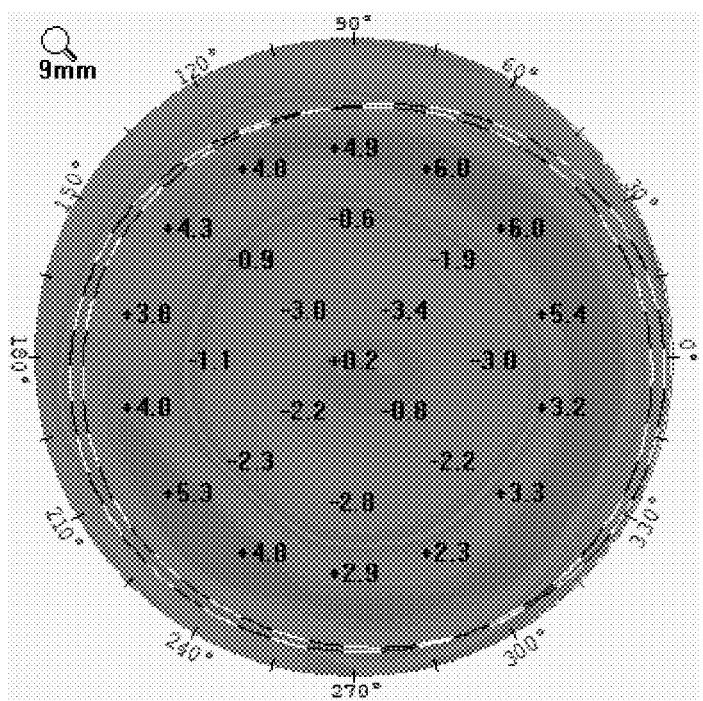
Figure 8C:
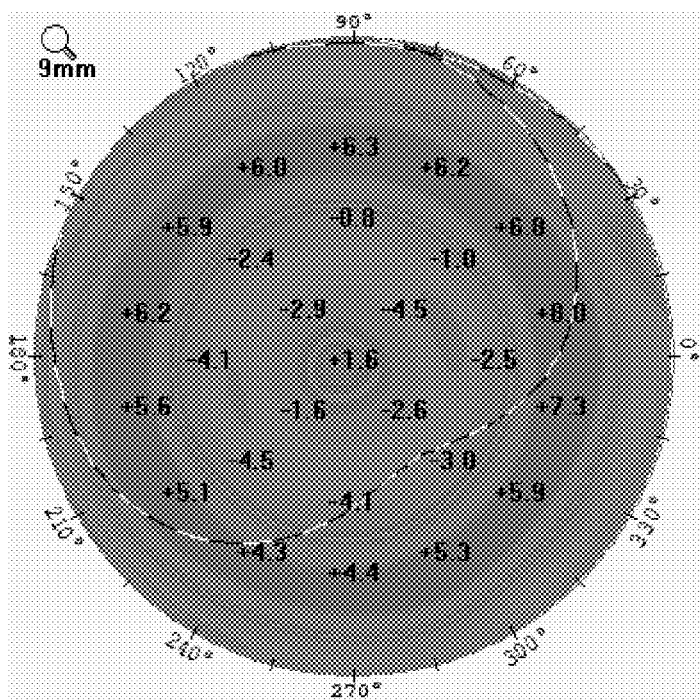
Figure 8D:
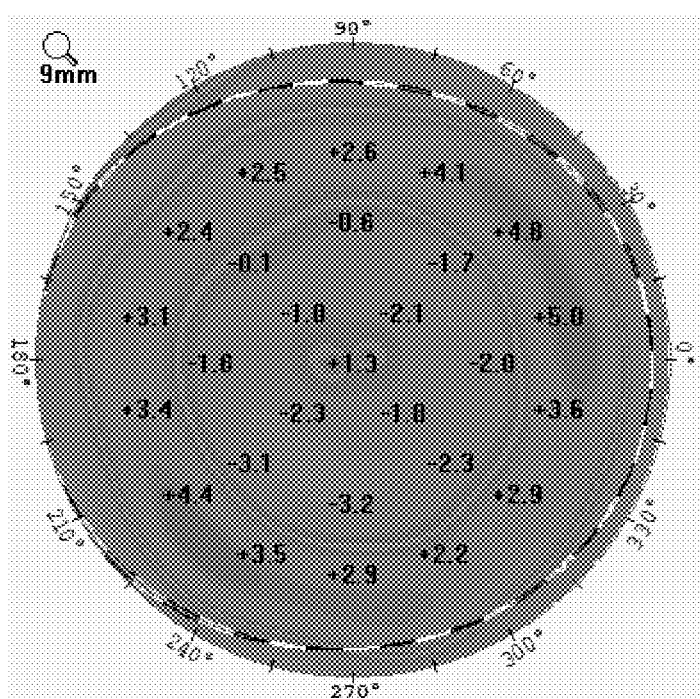
Figure 8E:
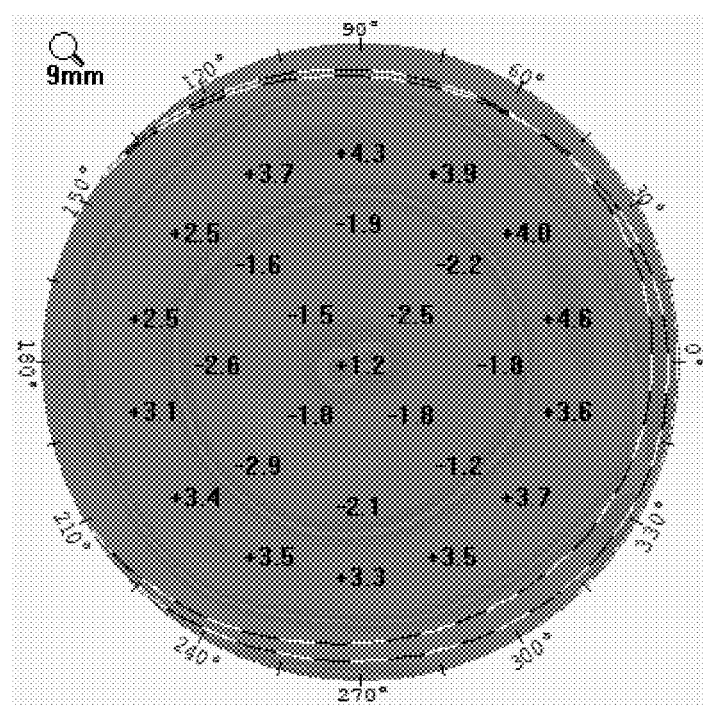
Figures 9A, 9B:
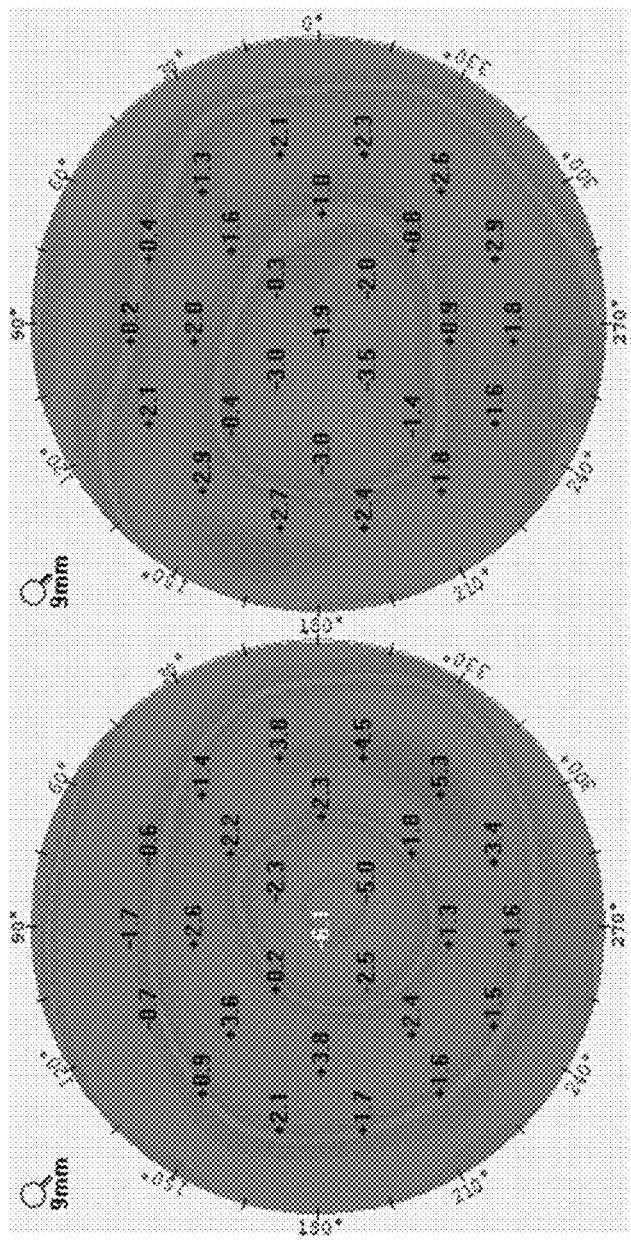
FIGS. 9A-E illustrate curvature change resulting from treatments of five eyes where the epithelium layer is entirely removed (epi-off), according to aspects of the present disclosure.
Figures 9C, 9D, 9E:
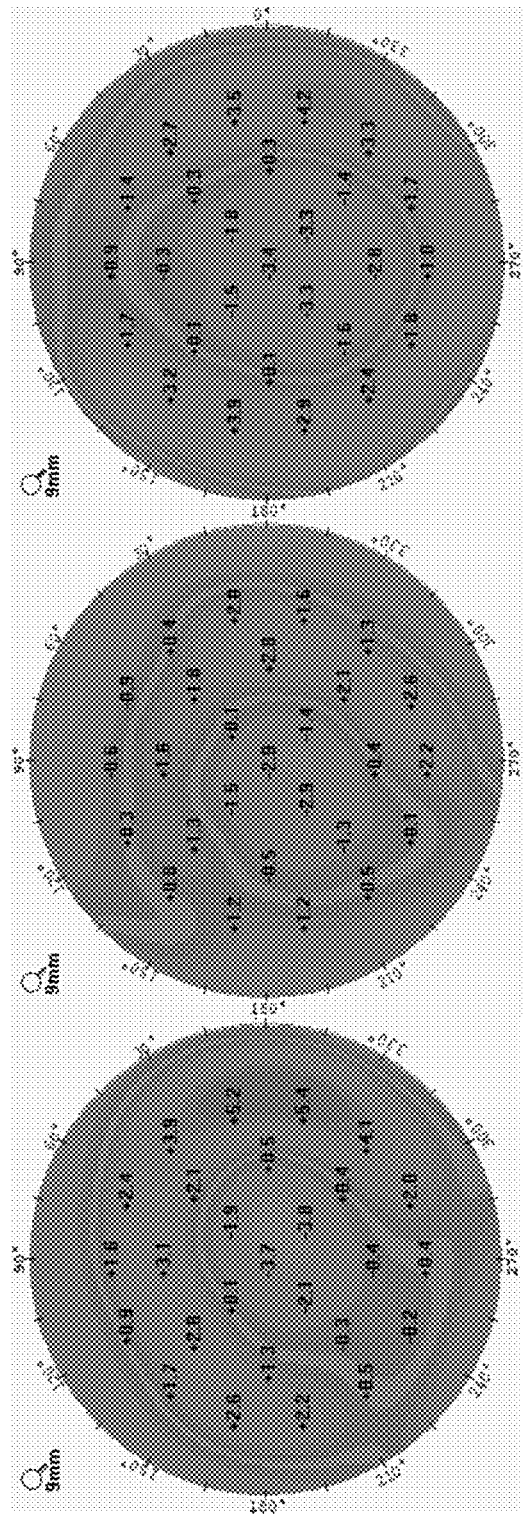

FIG. 7 illustrates oxygen concentration and fluorescent intensity indicating the presence of the cross-linking agent at a location during an example treatment. Laser scanning is optimized based on experiments on ex-vivo porcine eyes. In particular, the dose is 15 J/cm$^2$, the treatment time is 18 min, and the laser power is 1.75 mW. The circular treatment zone has a 4 mm diameter and the scan pattern covers the treatment zone fully (full pitch). Oxygen is measured under a 200 µm flap. The fluorescent intensity is measured by averaging 520-540 nm wavelengths. FIG. 7 shows that 8 Hz repetition frequency provides a good balance between oxygen depletion and replenishment at each repetition cycle, so that the oxygen level at the depth of 200 µm is still slightly above zero. The drug is consumed during the treatment, and the rate of drug destruction by the laser beam is negligible.

Correspondingly, FIGS. 8A-E show the curvature change resulting from treatments of five eyes where the epithelium layer is left on the eye (epi-on). Meanwhile, FIGS. 9A-E show the curvature change resulting from treatments of five eyes where the epithelium layer is entirely removed (epi-off). The experimental results indicate that laser scanning with the parameters above and a repetition frequency of 8 Hz provides greater flattening than treatments than treatments using UV LED.

As described above, the rate of corneal cross-linking activity is limited by oxygen concentrations in the corneal tissue. Thus, embodiments can optimize parameters for laser scanning to achieve scan patterns that affect depletion/replenishment of oxygen for cross-linking activity. In an example implementation, a pulsed laser beam is scanned over corneal tissue with a 50% duty cycle and a fixed pulse frequency. As the laser beam scans a pattern, the laser beam leaves unexposed regions of corneal tissue before and after each exposed region along the scan. The exposed regions receive photoactivating light from the laser beam, and the resulting cross-linking activity depletes oxygen in the exposed region. Advantageously, the adjacent unexposed regions enhance the diffusion of oxygen back into an exposed region after the laser beam leaves the exposed region. The pattern scanned by the laser beam can be dithered back and forth to ensure that cross-linking activity is generated over the entire desired treatment area. In some cases, the pulse may be selected based on the scan velocity to expose a region of corneal tissue approximately equal to the diameter of the laser beam at a time.

Figure 19A:
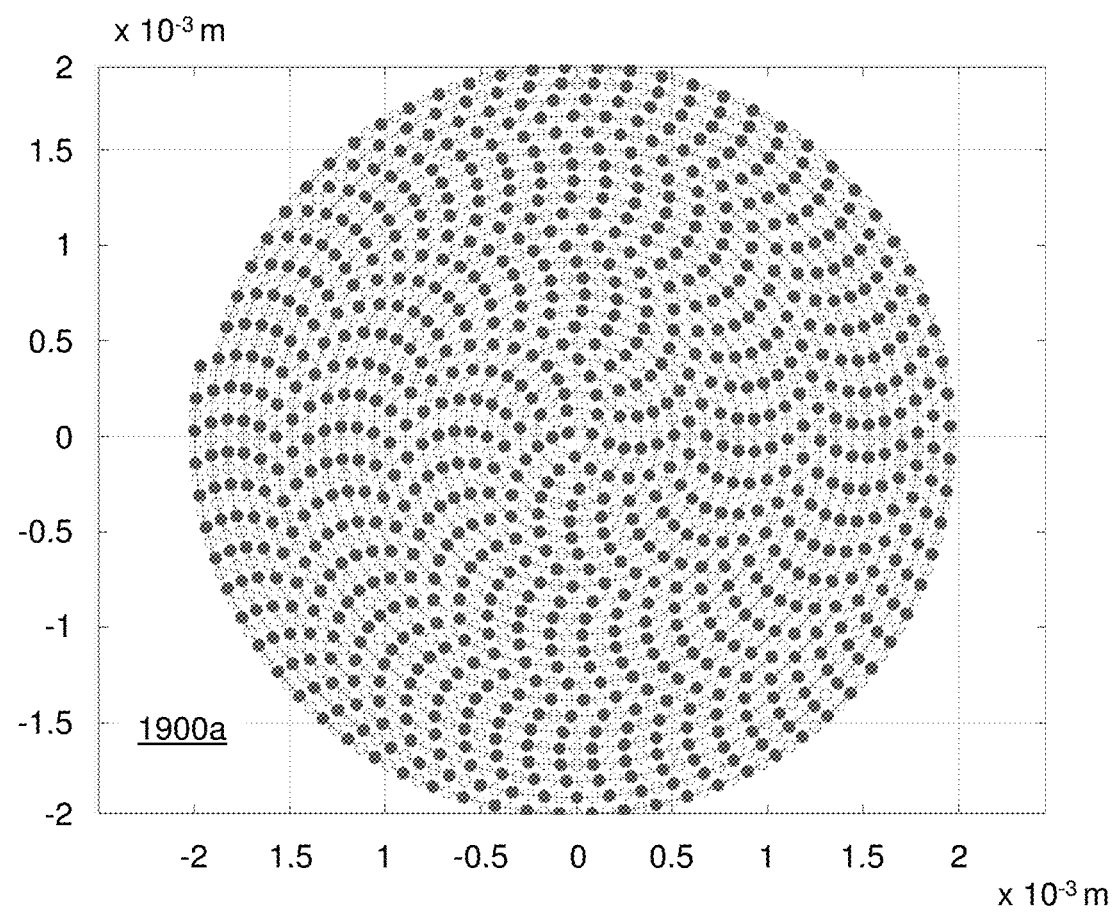
FIG. 19A illustrates an example annular treatment pattern with an outer diameter of approximately 4 mm, produced by pulsing a laser beam at a 50% duty cycle and a fixed pulse frequency over a spiral tracing, according to aspects of the present disclosure.
Figure 19B:
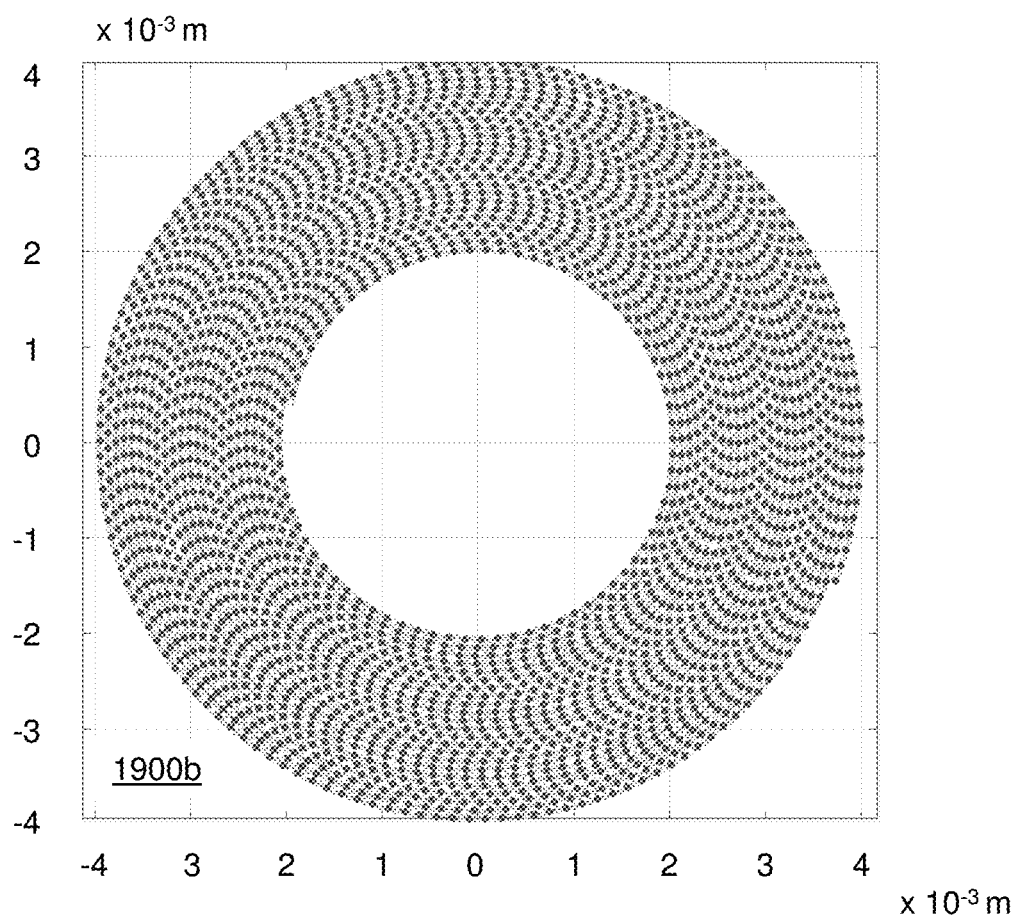
FIG. 19B illustrates an example annular treatment pattern with an outer diameter of approximately 8 mm, produced by pulsing a laser beam at a 50% duty cycle and a fixed pulse frequency over a spiral tracing, according to aspects of the present disclosure.

FIG. 19A illustrates an example annular treatment pattern 1900a with an outer diameter of approximately 4 mm. FIG. 19B illustrates an example annular treatment pattern 1900b with an outer diameter of approximately 8 mm. The treatment patterns 1900a, b are produced by pulsing a laser beam at a 50% duty cycle and a fixed pulse frequency over a spiral scan (spiraling inwardly toward a center). The shaded spots indicate the exposed regions where the laser beam is "on" and the unshaded spots indicate the adjacent unexposed regions where the laser beam is "off." The size of the exposed regions is determined by pulse frequency and scan velocity.

To produce the patterns 1900a, b, the formulas relating to scan parameters may be given by the following:

Input:
$D_{min}$—inner diameter of annular treatment pattern
$D_{max}$—outer diameter of annular treatment pattern
$P_r$—pitch in radial direction
$f_{upd}$—update frequency
$\theta_0$—initial spiral angle (changing $\theta_0$ rotates the spiral)

Formulas:
spiral update time:

$$t_{upd} = \frac{1}{f_{upd}} \quad (1)$$

spiral length:

$$L_{sp} = \frac{\pi \cdot (D_{max}^2 - D_{min}^2)}{4 \cdot P_r} \quad (2)$$

linear velocity:

$$V = f_{upd} \cdot L_{sp} \quad (3)$$

time constant (for spiral formula below):

$$\tau = \frac{t_{upd}}{1 - \left(\frac{D_{min}}{D_{max}}\right)^2} \quad (4)$$

spiral angle (for spiral formula below):

$$\theta_{sp} = \sqrt{V \cdot \frac{4\pi\tau}{P_r}} \quad (5)$$

number of loops:

$$N_{Lps} = (D_{max} - D_{min})/(2 \cdot P_r) \quad (6)$$

spiral formula ($t \in [0, t_{upd}]$):

$$\theta(t) = \theta_0 + \theta_{sp} - \sqrt{V \cdot \frac{4\pi(\tau - t)}{P_r}} \quad (7)$$

$$r(t) = \sqrt{V \cdot P_r \cdot (\tau - t)/\pi} \quad (8)$$

$$r(t) = \frac{P_r}{2\pi} \cdot (\theta_0 + \theta_{sp} - \theta(t)) \quad (9)$$

$$\theta(0) = \theta_0 \quad (10)$$

$$r(0) = D_{max}/2 \quad (11)$$

$$r(t_{upd}) = D_{min}/2 \quad (12)$$

wave formula:

$$x(t) = r(t) \cdot \cos(\theta(t)) \quad (13)$$

$$y(t) = r(t) \cdot \sin(\theta(t)) \quad (14)$$

In another example implementation, a pulsed laser beam may be scanned over corneal tissue with a 50% duty cycle and a variable pulse frequency so that the laser beam leaves unexposed regions of corneal tissue on all four sides of each exposed region in the resulting pattern. The resulting pattern resembles a checkerboard. Advantageously, compared to the laser beam with fixed pulsed frequency described above, the adjacent unexposed regions of corneal tissue on all four sides of an exposed region promotes greater diffusion of oxygen back into the exposed region after the laser beam leaves the exposed region. The pulse frequency can be varied between predefined minimum and maximum values, resulting in corresponding minimum and maximum exposure regions.

Figure 20A:
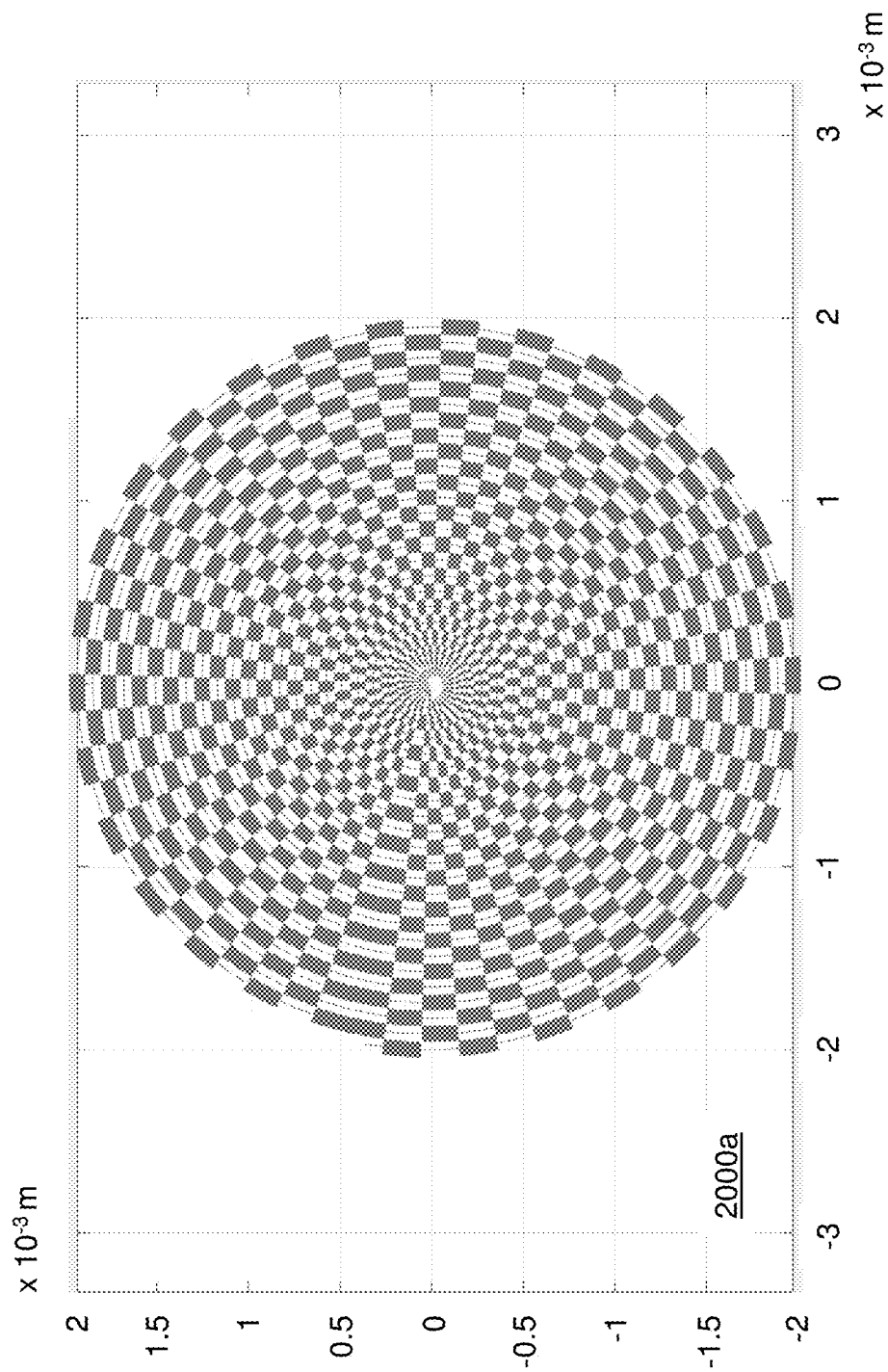
FIG. 20A illustrates an example annular treatment pattern with an outer diameter of approximately 4 mm, produced by pulsing a laser beam at a 50% duty cycle and a variable pulse frequency over a spiral tracing, according to aspects of the present disclosure.
Figure 20B:
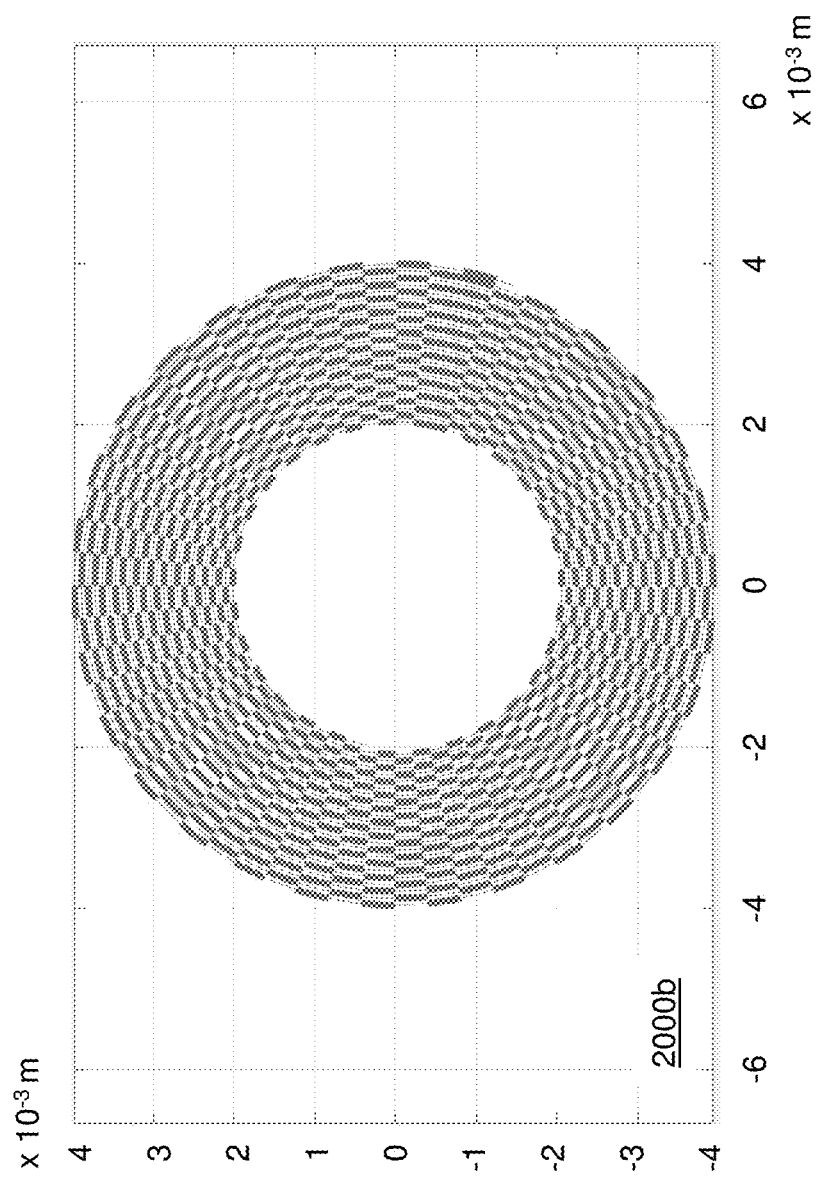
FIG. 20B illustrates an example annular treatment pattern with an outer diameter of approximately 8 mm, produced by pulsing a laser beam at a 50% duty cycle and a variable pulse frequency over a spiral tracing, according to aspects of the present disclosure.

FIG. 20A illustrates an example annular treatment pattern 2000a with an outer diameter of approximately 4 mm. FIG. 20B illustrates an example annular treatment pattern 2000b with an outer diameter of approximately 8 mm. The treatment patterns 2000a, b are produced by pulsing a laser beam at a 50% duty cycle and a variable pulse frequency over a spiral pattern (spiraling inwardly toward the center). The shaded regions in FIGS. 20A-B indicate the exposed regions where the laser beam is "on" and the unshaded regions indicate the adjacent unexposed regions where the laser beam is "off."

To produce the patterns 2000a, b, the formulas relating to scan parameters may be given by the following:

Input:
DC—duty cycle
$N_{sct}$—number of sectors over $2\pi$ rad angle

Formulas:
angular pitch:

$$\Delta\theta = 2\pi/N_{sct} \quad (15)$$

number of spots:

$$N_{spt} = \text{round}\left(\frac{\theta(\tau_{upd}) - \theta_0}{\Delta\theta}\right) + 1 \quad (16)$$

spot counter:

$$nsp = 1, 2, \ldots, N_{spt} \quad (17)$$

meridional angles:

$$\theta m_{nsp} = \theta_0 + (nsp - 1) \cdot \Delta\theta \quad (18)$$

loop numbers (may be fractional):

$$nLp_{nsp} = \frac{(nsp-1) \cdot \Delta\theta}{2\pi} \quad (19)$$

even/odd loop index (in the range from −1 to 1):

$$ii_{nsp} = rem(nLp_{nsp}, 2) - 1 \quad (20)$$

laser on angle:

$$\theta on_{nsp} = \theta m_{nsp} + ii_{nsp} \cdot \Delta\theta/2 \quad (21)$$

laser off angle:

$$\theta off_{nsp} = \theta on_{nsp} + \Delta\theta \cdot DC \quad (22)$$

laser on time:

$$ton_{nsp} = \tau - \frac{P_r}{4\pi \cdot V} \cdot (\theta_0 + \theta_{sp} - \theta on_{nsp})^2 \quad (23)$$

laser off time:

$$toff_{nsp} = \tau - \frac{P_r}{4\pi \cdot V} \cdot (\theta_0 + \theta_{sp} - \theta off_{nsp})^2 \quad (24)$$

instantaneous laser modulation frequency:

$$f_{Las}(t) = \frac{V}{\Delta\theta \cdot r(t)} \quad (25)$$

Implementations of the laser beam with variable pulse frequency may employ a laser modulation signal that sets laser on/off times to coincide with a predefined number of meridians in the treatment pattern.

The size of the exposed regions is determined by pulse frequency and scan velocity, but the pulse frequency may vary in relation to the radial position of the laser beam. In particular, the modulation signal may have a variable frequency that increases toward the center of the spiral. The instantaneous laser modulation frequency is given by equation (25), where the linear velocity is given by equation (3). The radial pitch of the laser modulation is not constant.

Figure 20C:
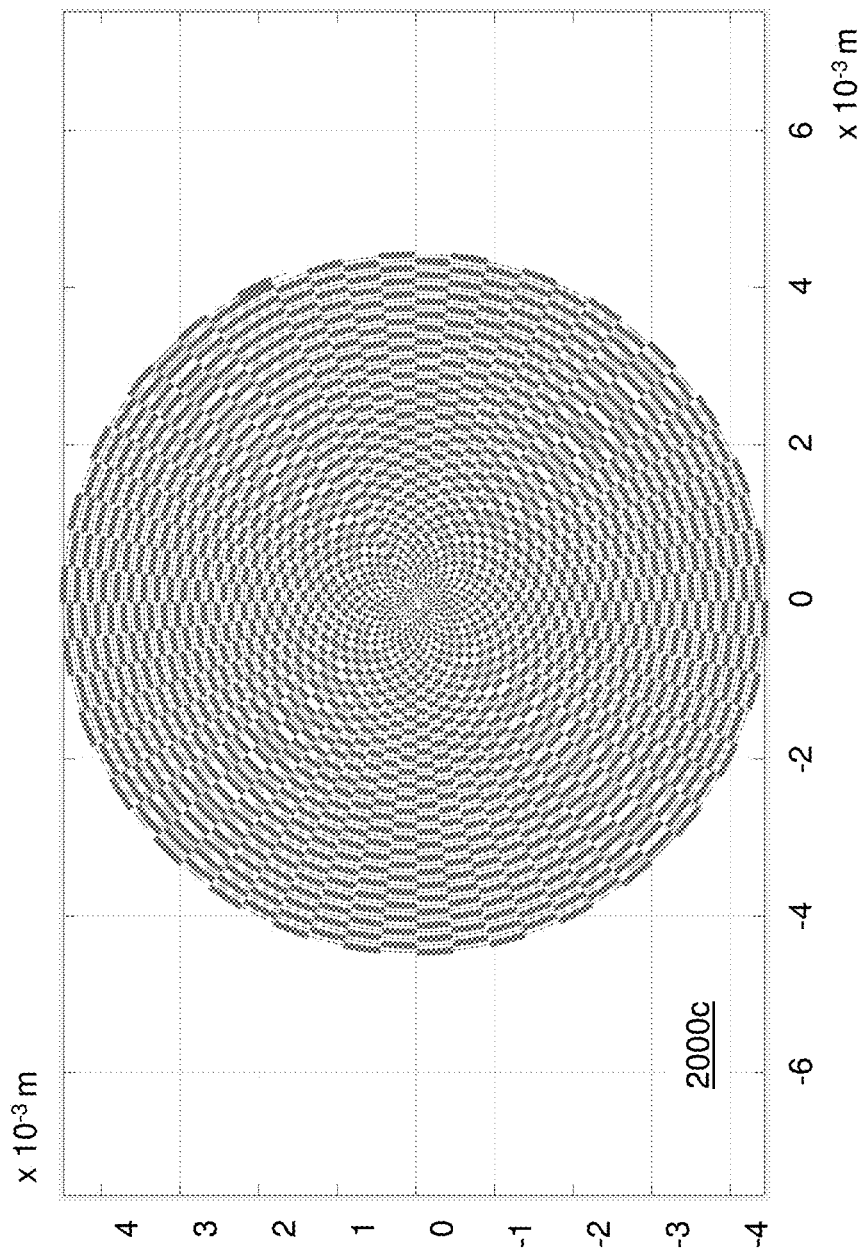
FIG. 20C illustrates an example annular treatment pattern with an outer diameter of approximately 9 mm, produced by a laser beam with variable pulse frequency, according to aspects of the present disclosure.

When implementing the laser beam with variable pulse frequency, the exposed regions may become smaller and smaller as the laser beam approaches the center of the treatment pattern. FIG. 20C illustrates an example annular treatment pattern 2000c with an outer diameter of approximately 9 mm, produced by a laser beam with variable pulse frequency. The shaded regions in FIG. 20C indicate the exposed regions where the laser beam is "on" and the unshaded regions indicate the unexposed regions where the laser beam is "off." As shown particularly in FIG. 20C, a tiered set of meridians may be employed to keep the exposed regions within a predefined range of sizes.

Figure 21:
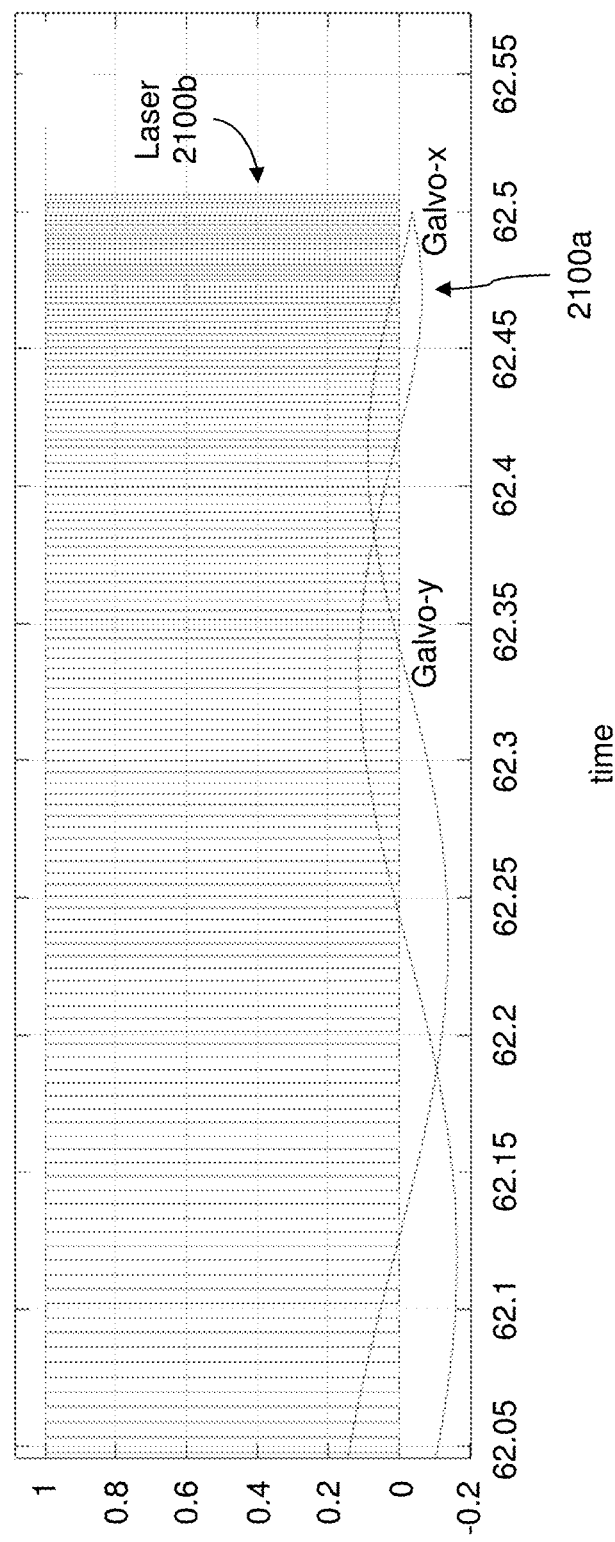
FIG. 21 illustrates example waveforms for driving a galvanometer as well as a laser modulation waveform during a portion of a treatment employing laser scanning, according to aspects of the present disclosure.

The laser modulation signal is synchronized with the drive signal for the galvanometer—the laser modulation signal can reset and alternate at each spiral restart. FIG. 21 illustrates example waveforms 2100a (Galvo-x, Galvo-y) for driving a galvanometer as well as a laser modulation waveform 2100b during a portion of a cross-linking treatment. As shown in FIG. 21, the laser modulation frequency varies with time and becomes greater as the laser beam spirals inwardly toward the center of the pattern. Meanwhile, the instantaneous laser duty cycle remains at a constant 50%.

Figure 22A:
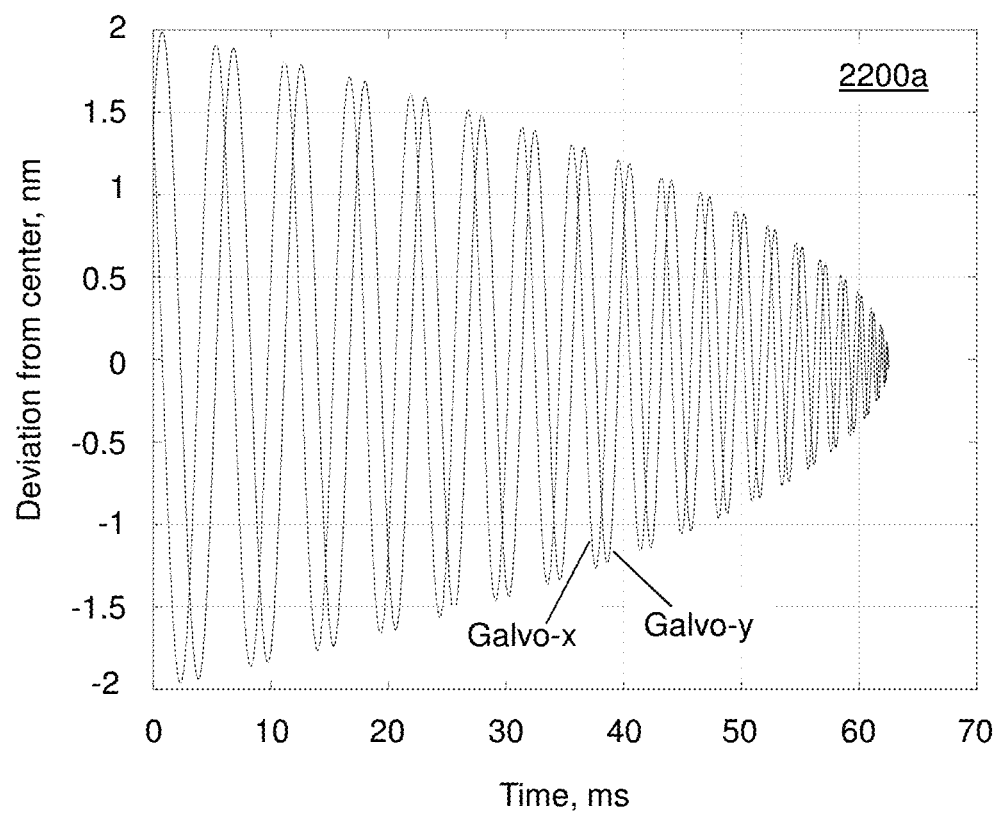
FIG. 22A illustrates example waveforms for driving a galvanometer during a complete treatment, according to aspects of the present disclosure.
Figure 22B:
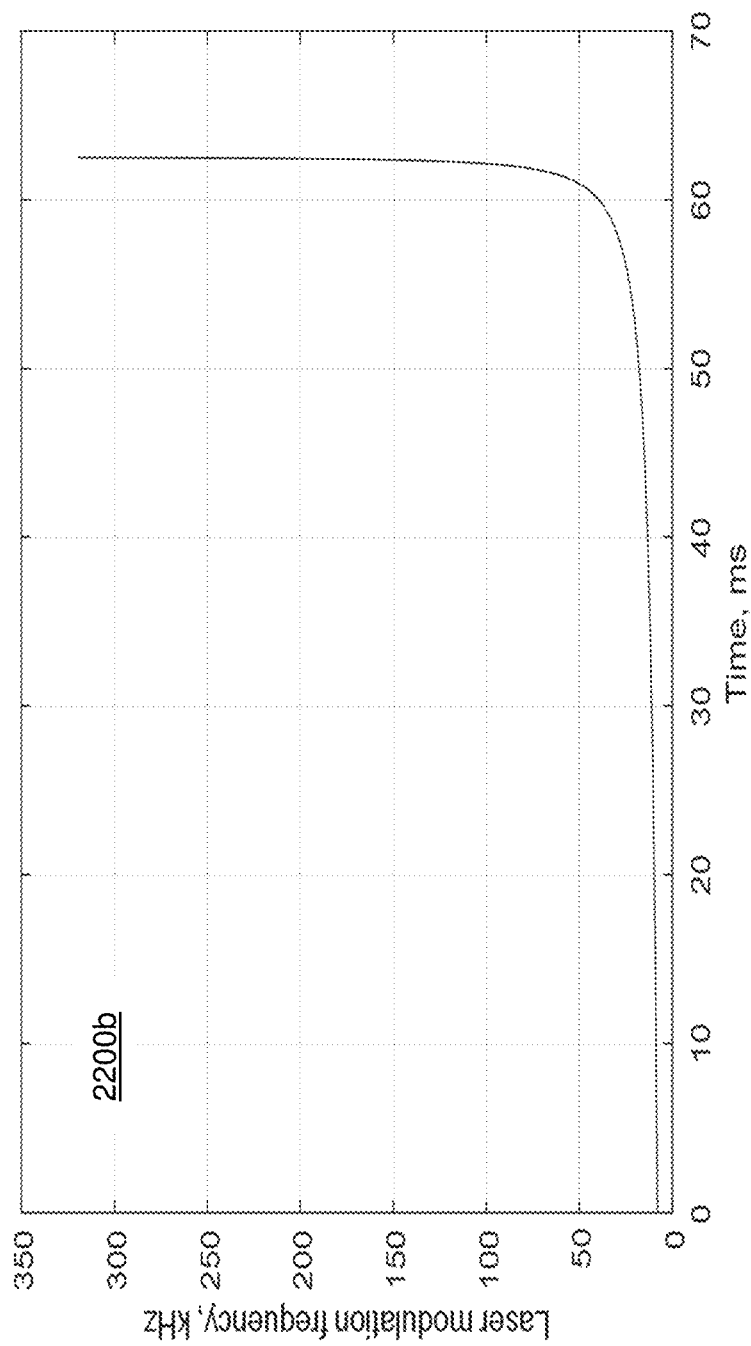
FIG. 22B illustrates a laser modulation waveform for the treatment of FIG. 22A, according to aspects of the present disclosure.

FIG. 22A illustrates example waveforms 2200a (Galvo-x, Galvo-y) for driving a galvanometer during a complete cross-linking treatment. Correspondingly, FIG. 22B illustrates a laser modulation waveform 2200b during the complete treatment. The laser modulation frequency increases rapidly near the end of the scan when the laser beam is near the center of the treatment pattern. This may cause the exposed tissue area to become too small near the center and can also increase the complexity of the electronic circuitry needed to drive the laser.

Figure 23:
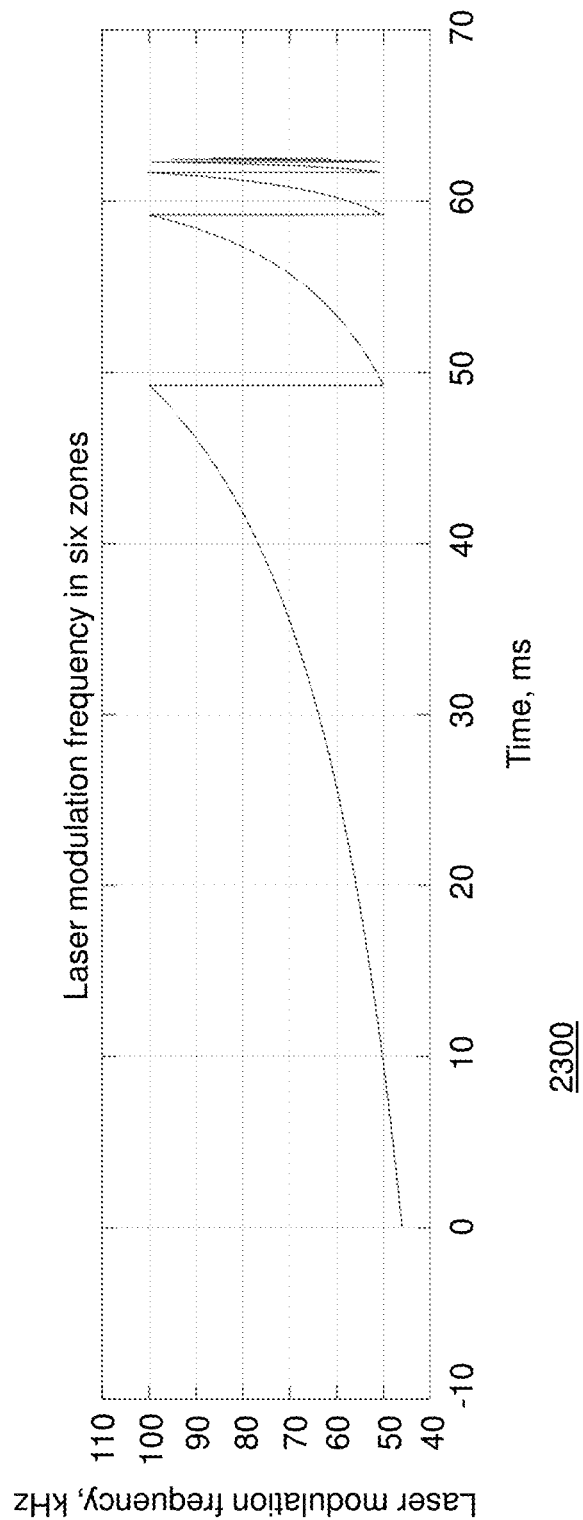
FIG. 23 illustrates an example laser modulation waveform split into multiple radial zones, according to aspects of the present disclosure.

To overcome the potential problem of undesirably high laser modulation frequencies near the center of the treatment pattern, the checkerboard angular pattern can be split into multiple radial zones based on the instantaneous laser modulation frequency. FIG. 23 illustrates an example laser modulation waveform 2300 implementing such an approach. In the outermost zone, the sector angle has a predefined value and the laser modulation frequency increases as the laser moves inwardly. As soon as the modulation frequency reaches a predefined limit, the sector angle doubles and the modulation frequency halves at the onset of the second zone. Subsequent zones are introduced in the same way. The number of zones is determined automatically to keep the modulation frequency below the predefined limit. (Thus, this approach may be referred herein as an "auto zone" approach.) Initial number of sectors (in the first zone) is a power of two, and the number of sectors halves when switching to the next zone.

TABLE 1 illustrates example output data for an annular pattern produced by (i) a pulsed laser beam scanned with fixed laser modulation frequency, (ii) a pulsed laser beam scanned with variable laser modulation frequency not implementing the auto zone approach, and (iii) a pulsed laser beam scanned with variable laser modulation frequency employing the auto zone approach.

TABLE 1

| Parameter | Fixed Laser Frequency | Variable Laser Frequency (not auto zone) | Variable Laser Frequency (auto zone) |
|---|---|---|---|
| Number of zones | 1 | 1 | 6 |
| Number of spots | 6361 | 1114 | 3993 |
| Spiral length, mm | 636.1 | 636.1 | 636.1 |
| Scan velocity, m/s | 10.2 | 10.2 | 10.2 |
| Minimum spot scan length, μm | 50 | 6.0 μm | 50.7 |
| Maximum spot scan length, μm | 50 | 565.6 | 110.5 |
| Minimum laser modulation frequency, kHz | 101.8 | 9.0 | 46.1 |
| Maximum laser modulation frequency, kHz | 101.8 | 809.9 | 100.2 |
| Minimum pulse width, μs | 4.9 | 0.62 | 5 |

The common input parameters for the patterns in TABLE 1 include:
 inner diameter of pattern: 100 μm
 outer diameter of patter: 9 mm
 laser beam (spot) diameter: 100 μm
 radial pitch: 100 μm
 update frequency: 16 Hz
 duty cycle: 50%

For the pulsed laser beam scanned with fixed laser modulation frequency, the input further includes a tangential pitch equal to 100 μm. For the pulsed laser beam scanned with variable laser modulation frequency not implementing the auto zone approach, the input further includes a number of sectors equal to 25. For the pulsed laser beam scanned with variable laser modulation frequency implementing the auto zone approach, the input further includes an initial number of sectors equal to 128 and a modulation frequency limit equal to 100 kHz.

Figure 24A:
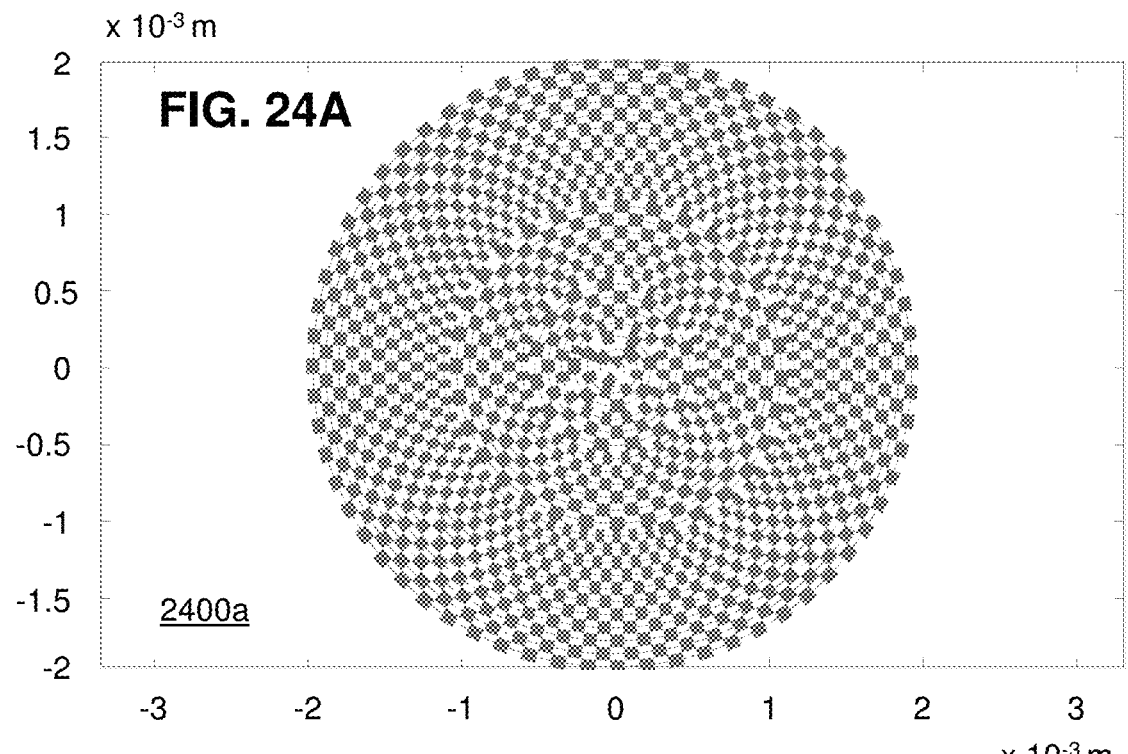
FIG. 24A illustrates an example annular treatment pattern with an outer diameter of approximately 4 mm, produced with a pulsed laser beam scanned with variable laser modulation frequency implementing a laser modulation waveform split into multiple radial zones based on a modulation frequency limit, according to aspects of the present disclosure.
Figure 24B:
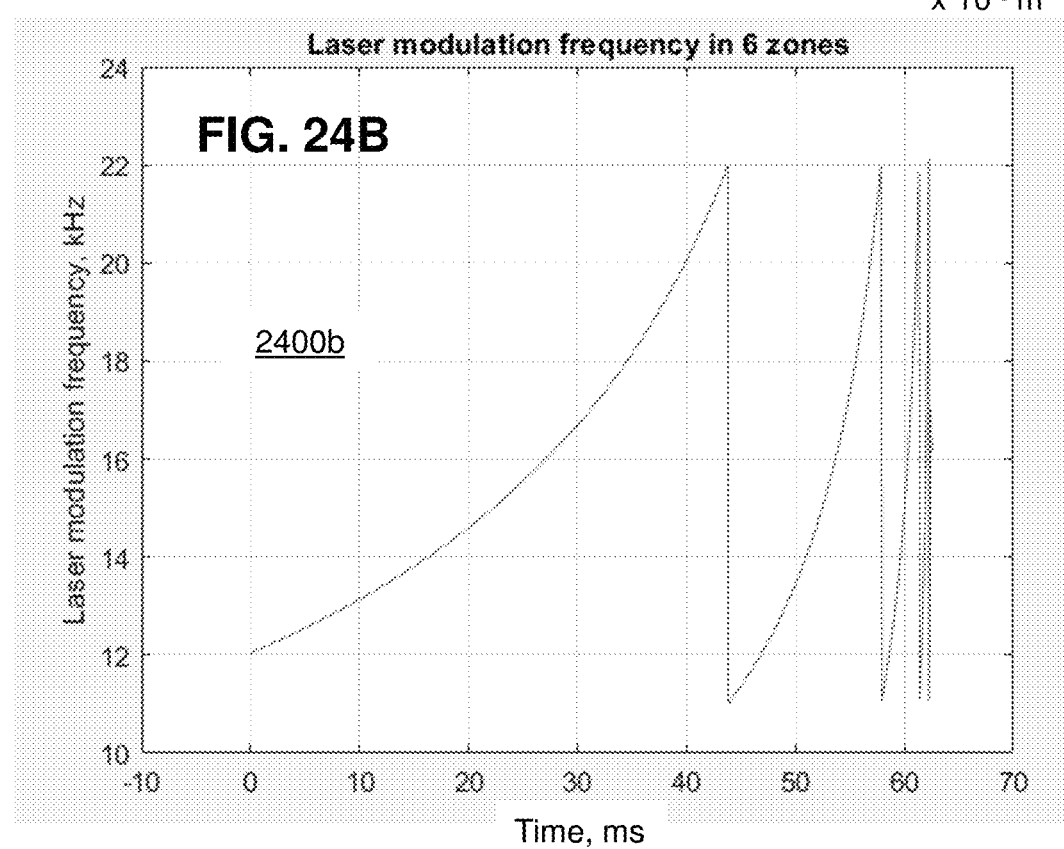
FIG. 24B illustrates the example laser modulation waveform split into multiple radial zones based on a modulation frequency limit for the treatment of FIG. 24A, according to aspects of the present disclosure.

FIG. 24A illustrates an example annular treatment pattern 2400a with an outer diameter of approximately 4 mm, produced with a pulsed laser beam scanned with variable laser modulation frequency implementing the auto zone approach (i.e., laser modulation waveform split into multiple radial zones based on a modulation frequency limit). FIG. 24B illustrates an example laser modulation waveform 2400b corresponding to the treatment pattern 2400a.

Figure 25A:
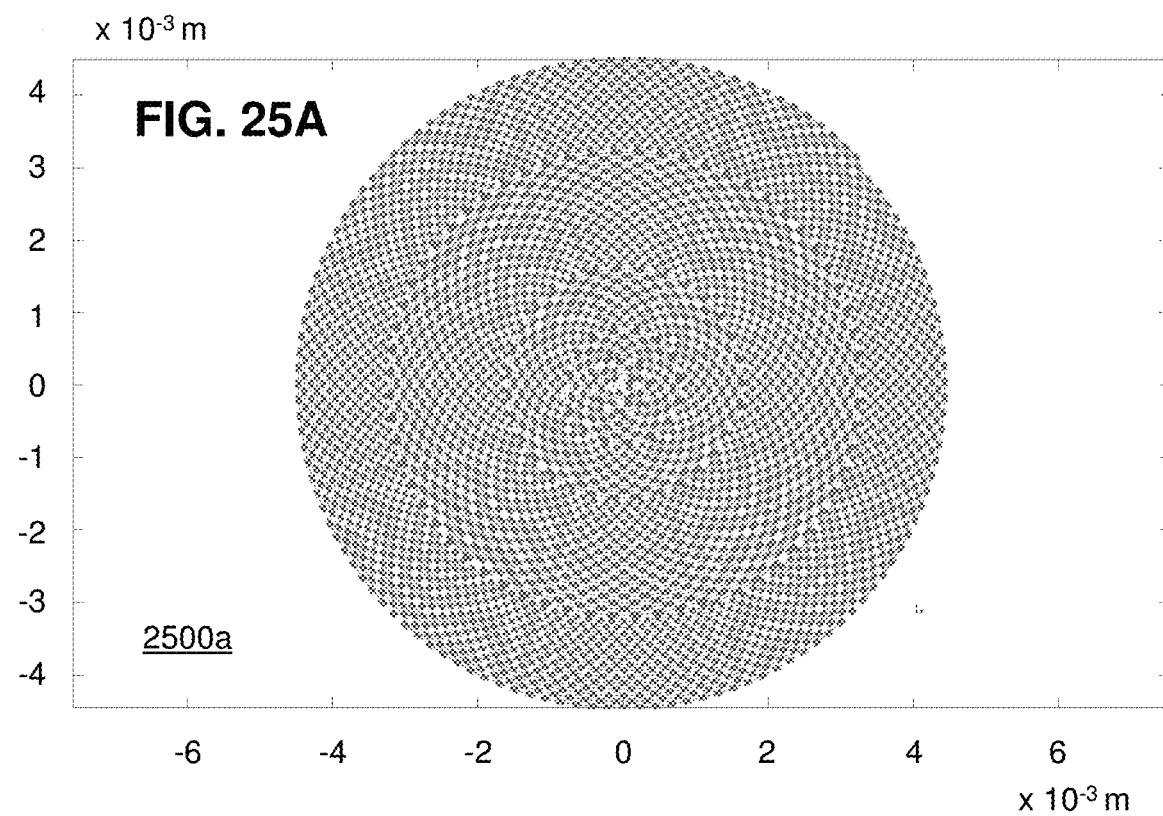
FIG. 25A illustrates an example annular treatment pattern with an outer diameter of approximately 9 mm, produced with a pulsed laser beam scanned with variable laser modulation frequency implementing a laser modulation waveform split into multiple radial zones based on a modulation frequency limit, according to aspects of the present disclosure.
Figure 25B:
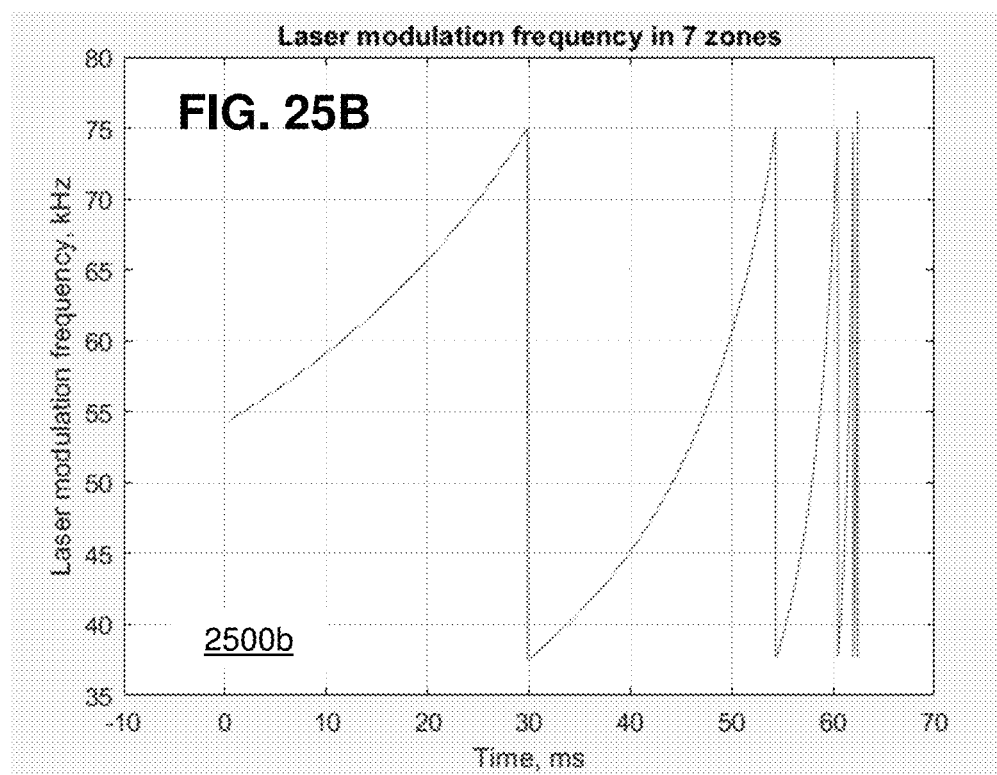
FIG. 25B illustrates the example laser modulation waveform split into multiple radial zones based on a modulation frequency limit for the treatment of FIG. 25A, according to aspects of the present disclosure.

The input parameters for the pattern 2400a include:
inner diameter of pattern: 85 μm
outer diameter of pattern: 4 mm
radial pitch: 85 μm
update frequency: 16 Hz
maximum number of meridians: 64
maximum modulation frequency: 22 kHz The output data for the pattern 2400a include:
number of zones: 6
spiral length: 147.8 mm
scan velocity: 2.3644 m/s
minimum modulation length: 52.4 μm
maximum modulation length: 107.2 μm
minimum laser modulation frequency: 11.014 kHz
maximum laser modulation frequency: 22.139 kHz FIG. 25A illustrates an example annular treatment pattern 2500a with an outer diameter of approximately 9 mm, produced with a pulsed laser beam scanned with variable laser modulation frequency implementing the auto zone approach. FIG. 25B illustrates an example laser modulation waveform 2500b corresponding to the treatment pattern 2500a.

Figure 26A:
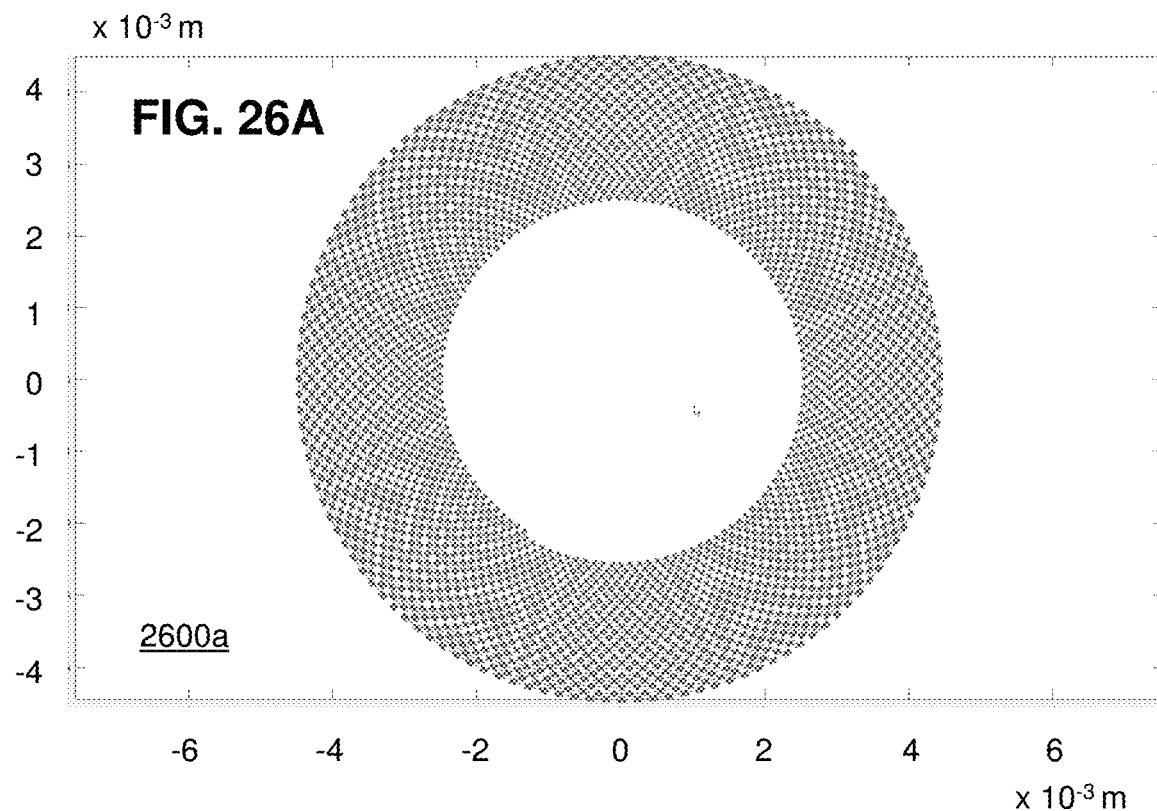
FIG. 26A illustrates an example annular treatment pattern 2600a with an outer diameter of approximately 9 mm produced with a pulsed laser beam scanned with variable laser modulation frequency implementing a laser modulation waveform with one radial zone based on a modulation frequency limit, according to aspects of the present disclosure.
Figure 26B:
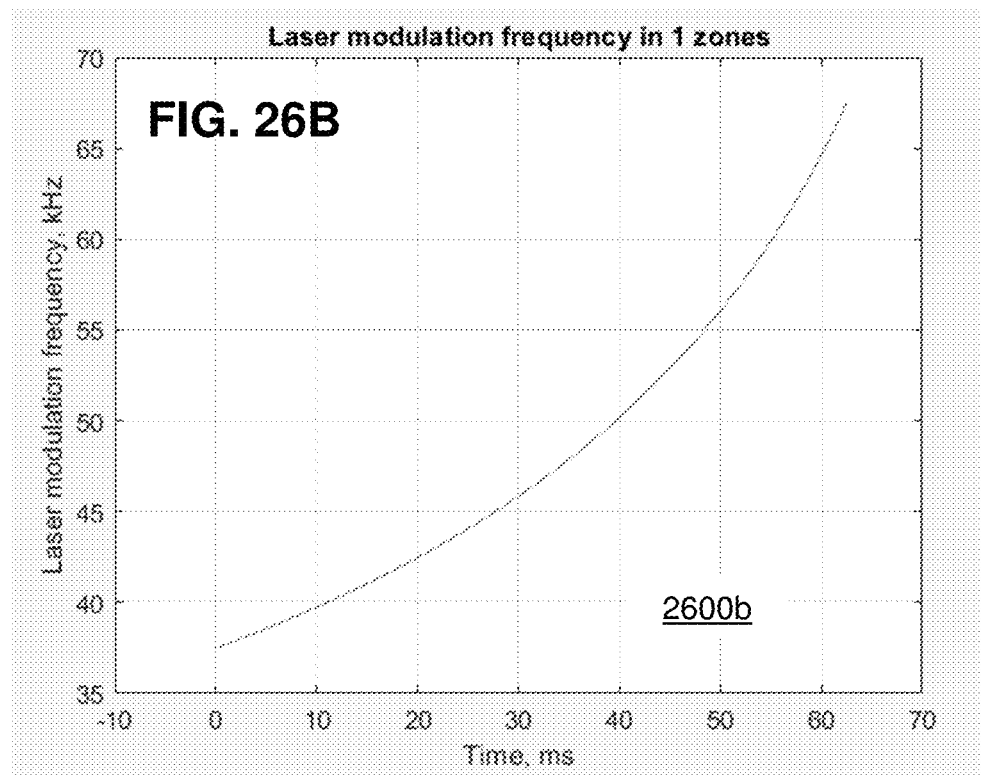
FIG. 26B illustrates the example laser modulation waveform with one radial zone based on a modulation frequency limit for the treatment of FIG. 25A, according to aspects of the present disclosure.

The input parameters for the pattern 2500a include:
inner diameter of pattern: 85 μm
outer diameter of pattern: 9 mm
radial pitch: 85 μm
update frequency: 16 Hz
maximum number of meridians: 128
maximum modulation frequency: 75 kHz The output data for the pattern 2500a include:
number of zones: 7
spiral length: 748.37 mm
scan velocity: 11.9739 m/s
minimum modulation length: 74.37 μm
maximum modulation length: 159.60 μm
minimum laser modulation frequency: 37.507 kHz
maximum laser modulation frequency: 76.225 kHz FIG. 26A illustrates an example annular treatment pattern 2600a with an outer diameter of approximately 9 mm, produced with a pulsed laser beam scanned with variable laser modulation frequency implementing the auto zone approach. FIG. 26B illustrates an example laser modulation waveform 2600b corresponding to the treatment pattern 2600a.

The input parameters for the pattern 2600a include:
inner diameter of pattern: 5 mm
outer diameter of pattern: 9 mm
radial pitch: 85 μm
update frequency: 16 Hz
maximum number of meridians: 128
maximum modulation frequency: 75 kHz The output data for the pattern 2600a include:
number of zones: 1
spiral length: 517.4 mm
scan velocity: 8.279 m/s
minimum modulation length: 61.34 μm
maximum modulation length: 110.45 μm
minimum laser modulation frequency: 37.47 kHz
maximum laser modulation frequency: 67.47 kHz
Although the auto zone approach is employed, the pattern includes only one zone.

Figure 27:
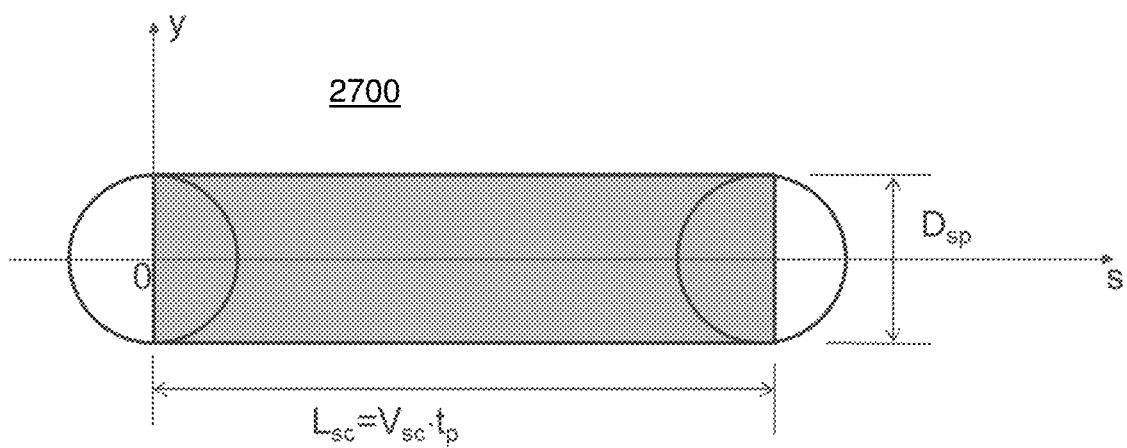
FIG. 27 illustrates aspects of a spot profile produced by a pulsed laser beam traveling along a scan, according to aspects of the present invention.

FIG. 27 illustrates aspects of a spot profile 2700 produced by a pulsed laser beam traveling along a scan s. As shown in FIG. 27, the laser beam has a laser spot diameter $D_{sp}$ and produces a scan length $L_{SC}$ which is a product of the scan velocity $V_{SC}$ and pulse width $t_p$.

Figure 28A:
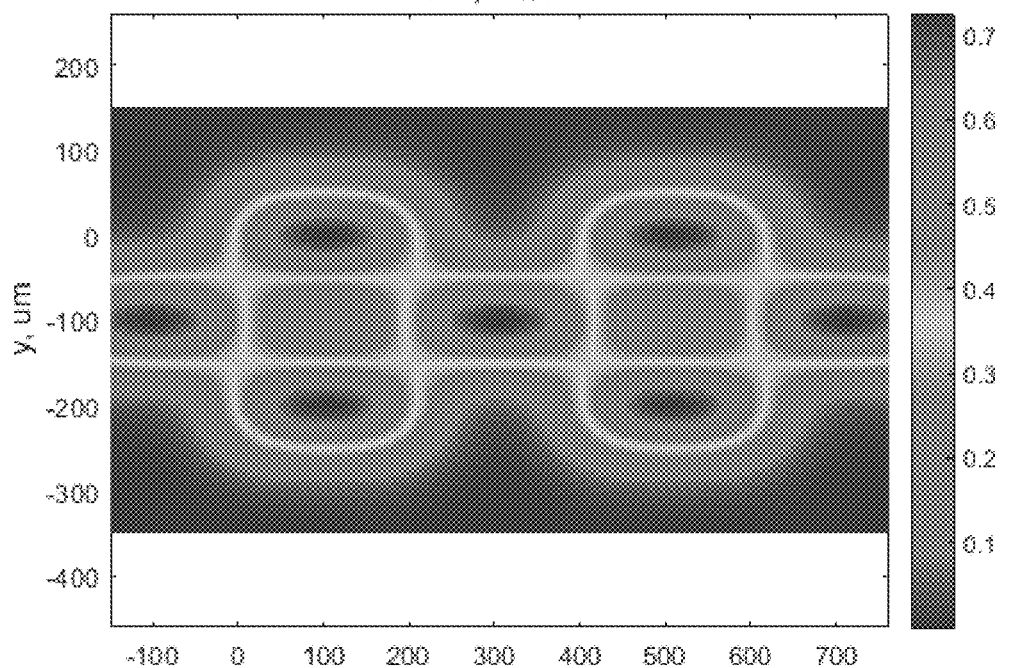
FIG. 28A illustrates a Gaussian laser spot with a laser modulation frequency of 25 kHz, according to aspects of the present invention.
Figure 28B:
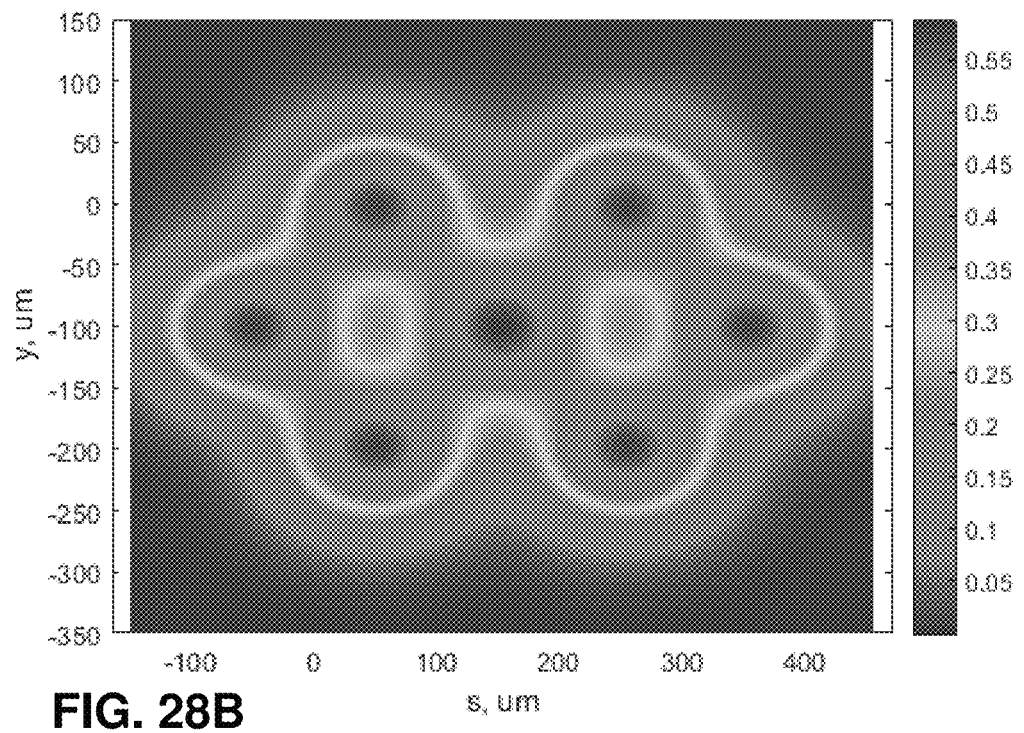
FIG. 28B illustrates a Gaussian laser spot with a laser modulation frequency of 50 kHz, according to aspects of the present invention.
Figures 28C, 28D:
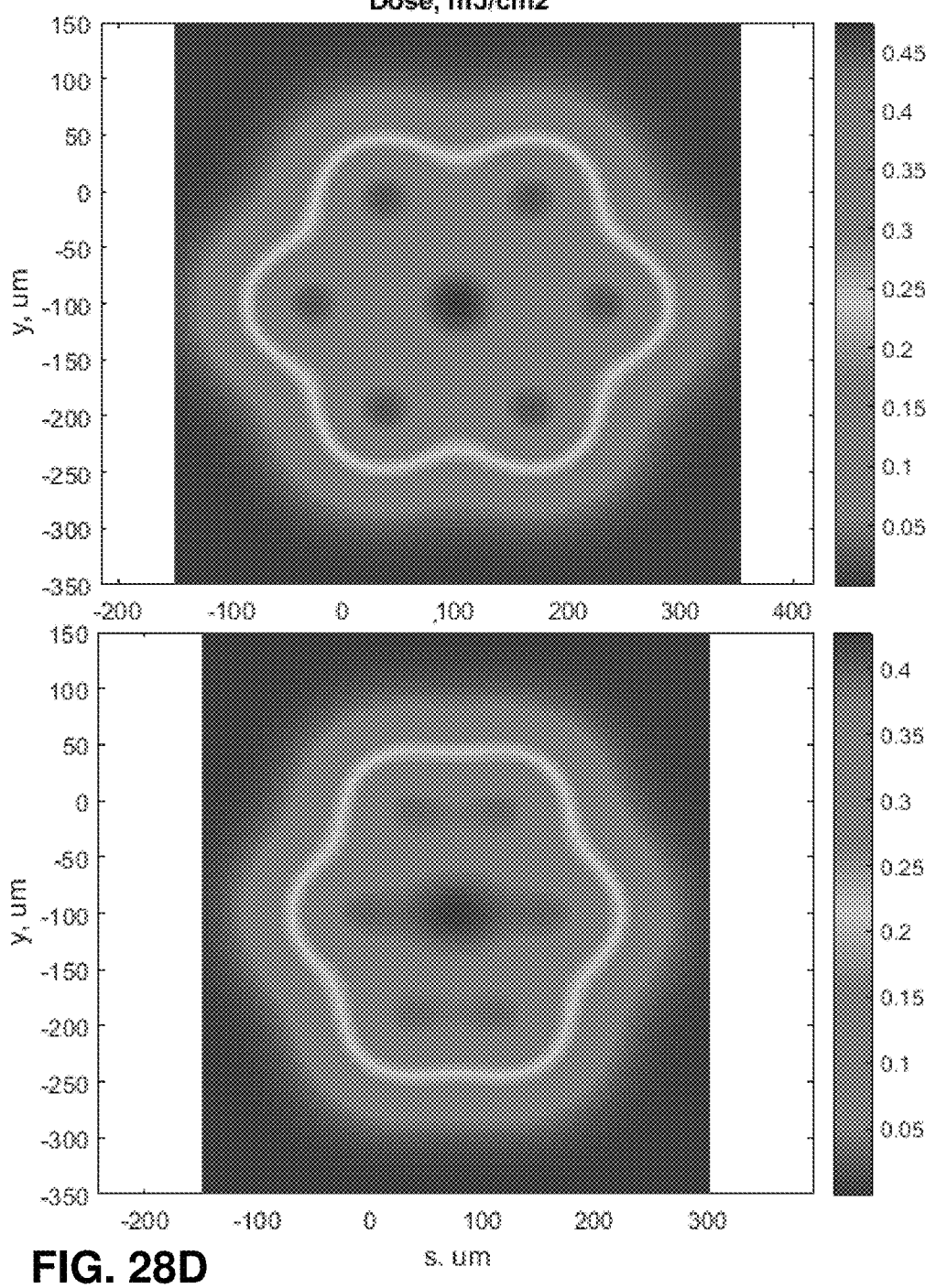
FIG. 28C illustrates a Gaussian laser spot with a laser modulation frequency of 75 kHz, according to aspects of the present invention.
FIG. 28D illustrates a Gaussian laser spot with a laser modulation frequency of 100 kHz, according to aspects of the present invention.

The following parameters may be employed to produce a pattern with an outer diameter of 9 mm, for instance:
scan velocity $V_{SC}$: 10.2 m/s
laser spot diameter $D_{sp}$: 100 μm
radial pitch: 100 μm
duty cycle: 50%
spot profile: flattop and Gaussian
laser power: 8 mW The modulation frequency can be optimized. In the case of a Gaussian laser beam, the modulation frequency is preferably less than 50 kHz to maintain sufficient contrast in dose between treated and untreated spots in a single scan. For instance, at 50 kHz, the contrast ((max min)/mean) is approximately 50%. This estimate depends on spot profile (inner and outer diameters) and galvanometer velocity. FIGS. 28A-D illustrate contrast as a function of modulation frequency. FIG. 28A illustrates a Gaussian laser spot with a laser modulation frequency of 25 kHz. FIG. 28B illustrates a Gaussian laser spot with a laser modulation frequency of 50 kHz. FIG. 28C illustrates a Gaussian laser spot with a laser modulation frequency of 75 kHz. FIG. 28D illustrates a Gaussian laser spot with a modulation frequency of 100 kHz.

TABLE 2A provides input parameters for producing various annular treatment patterns A-F via pulsed laser scanning implementing the auto zone approach. Correspondingly, TABLE 2B provides output data for the various treatment patterns A-F. The requirement imposed onto the patterns A-F is a minimum modulation length of 85 μm.

TABLE 2A

| Input Parameters | A | B | C | D | E | F |
| --- | --- | --- | --- | --- | --- | --- |
| Outer diameter, mm | 4 | 8 | 8 | 9 | 9 | 9 |
| Inner diameter, mm | 0.085 | 4 | 3 | 4 | 85 | 85 |
| Repetition Frequency, Hz | 16 | 16 | 16 | 16 | 8 | 16 |
| Pitch, μm | 85 | 85 | 85 | 85 | 85 | 85 |
| Maximum # of Meridians | 64 | 128 | 128 | 128 | 128 | 128 |
| Maximum Modulation Frequency, kHz | 13.75 | 41 | 47 | 48 | 35 | 70 |

TABLE 2B

| Output Data | A | B | C | D | E | F |
|---|---|---|---|---|---|---|
| Number of zones | 6 | 2 | 3 | 2 | 7 | 7 |
| Spiral length, mm | 147.8 | 443.519 | 508.20 | 517.44 | 748.37 | 748.37 |
| Scan velocity, m/s | 2.3644 | 7.0963 | 8.1312 | 8.279 | 5.987 | 11.9739 |
| Minimum modulation length, μm | 85.0 | 86.5 | 86.5 | 86.2 | 85.3 | 85.3 |
| Maximum modulation length, μm | 171.6 | 173.00 | 172.91 | 172.4 | 171.0 | 171.0 |
| Minimum laser modulation frequency, kHz | 6.88 | 20.51 | 23.51 | 24.01 | 17.50 | 35.00 |
| Maximum laser modulation frequency, kHz | 13.77 | 41.00 | 47.01 | 48.01 | 35.00 | 70.00 |
| Minimum pulse width, μs | 35.9714 | 12.1935 | 10.6356 | 10.414 | 14.2501 | 7.1251 |

Point and Shoot Laser Scanning Approach

As described above, aspects of a scan pattern may be defined by a plurality of discrete dots. A treatment pattern may be defined by scanning discrete dots in randomized manner or a semi-randomized manner based on continuous x, y variables.

Figure 10:
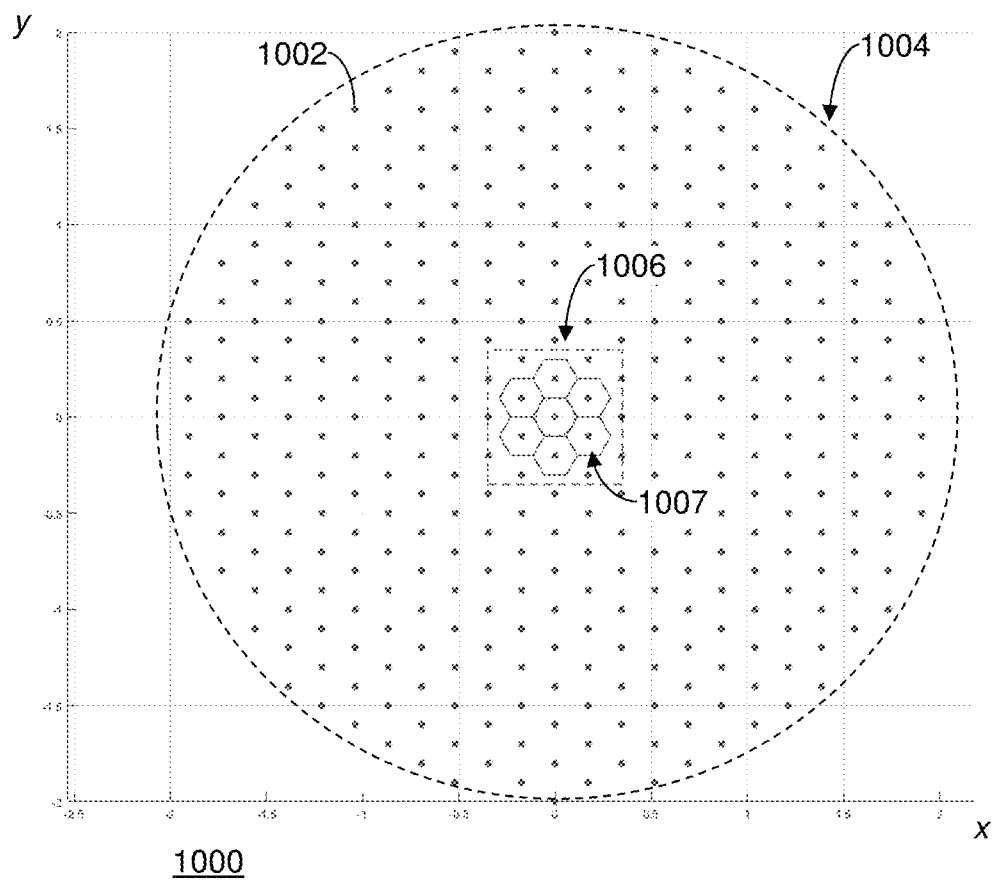
FIG. 10 illustrates aspects of an example scan pattern defined by discrete dots applied according to a grid inside a boundary defining a treatment zone, according to aspects of the present disclosure.

According to some embodiments, a point and shoot technique may be employed to apply a sequence of discrete dots and achieve a desired treatment zone. As shown in FIG. 10, a scan pattern 1000 may be defined by scanning discrete dots 1002 according to a grid 1006 inside a boundary 1004 (e.g., a circular boundary) defining the treatment zone. In particular, the grid 1006 includes an arrangement of hexagonal cells 1007, where the dots 1002 are sampled (shot) into the hexagonal cells 1007 by the laser beam. The hexagonal cells 1007 may be arranged to space the dots 1002 uniformly within the boundary 1004, i.e., to maximize homogeneity of the photoactivating light across the treatment zone. The size (e.g., diameter) of the laser beam spot and the pitch of the grid 1006 may be matched to maximize this homogeneity.

After the grid of the scan pattern has been defined, the order for shooting the laser beam spots into the cells of the grid can be optimized. The order of shots, duration of shots, intensity of shots, and the number of repeated shots into each cell may affect the efficiency of cross-linking activity and the desired amount of corneal shape change. According to one approach, each cell is sampled at least once in a random order. According to another approach, the treatment system tracks the total dose delivered to each cell based on the accumulation of shots received. In other words, the treatment system maintains a dose map as treatment progresses and determines where to deliver the next shot according to this dose map. During the treatment, the treatment system may deliver the next shot to the cell with the lowest total dose (which may be the cell that has received the fewest number of shots). If more than one cell has the lowest total dose, the treatment system may also select, for the next shot, a cell that is located the greatest distance from the cell receiving the previous shot. Selecting cells based on greatest distance between consecutive shots may provide more efficient and uniform cross-linking activity across the scan pattern. In particular, greater distance between shots may improve the local supply of oxygen for cross-linking at the next cell. Additionally, the effect of activity at the previous cell (cross-talk) is less likely to affect the activity at a next cell that is a greater distance away from the previous cell.

A possible downside of selecting cells to maximize distance between consecutive shots is the increased time between the applications of the consecutive shots due to the time to move across the distance (transit time). Accordingly, to address this possible downside, the treatment system may constrain the distance between consecutive shots, e.g., the distance is maximized but does not exceed a predefined maximum travel distance (MTD). Thus, the treatment system may choose a cell with the minimum total dose within the MTD. Where all cells have received the same dose or the same number of shots, the treatment system may select the next cell randomly.

In general, the point and shoot technique can be optimized according to various parameters to achieve the desired treatment. Such parameters include, but are not limited to: (i) size of the laser beam spot; (ii) pitch of the grid; (iii) number of shots per cell across the scan pattern (also known as visits); (iv) total treatment time; (v) irradiance of the laser beam; (vi) amount of time between application of consecutive dots; and/or (vi) the order in which the spots are applied. For instance, FIG. 11 illustrates different combinations of parameter values for treatments employing a hexagonal grid within a circular boundary (corresponding to the treatment zone) with a diameter of approximately 4 mm where the dose is 15 J/cm2 UVA light, the treatment time is approximately 1000 seconds, the time required to transit between consecutive spots is approximately 0.2 milliseconds, and the spot profile is Gaussian. The parameters in FIG. 11 include a size of the laser beam spot measured as a diameter $D_{sp}$ (μm) full width at half maximum (FWHM), a pitch of the grid (μm), number of visits (where a visit corresponds to a single pass of the scan pattern resulting in all cells receiving a shot), the number of spots across the scan pattern, the number of shots, the time for each visit (s), time for each shot (ms) (shooting time), peak irradiance (W/cm$^2$), power of the laser beam (mW), peak dose per shot (J/cm$^2$), and nonuniformity (%).

Figure 12A:
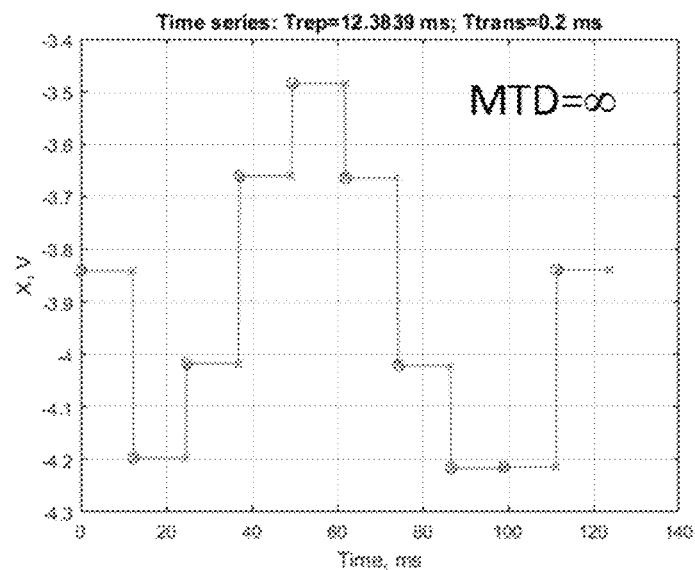
FIGS. 12A-C illustrate example time series of scanner position graphs for implementations of the combination of the treatment parameters shown in row B of FIG. 11 using different respective values for maximum travel distance (MTD), according to aspects of the present disclosure.
Figure 12B:
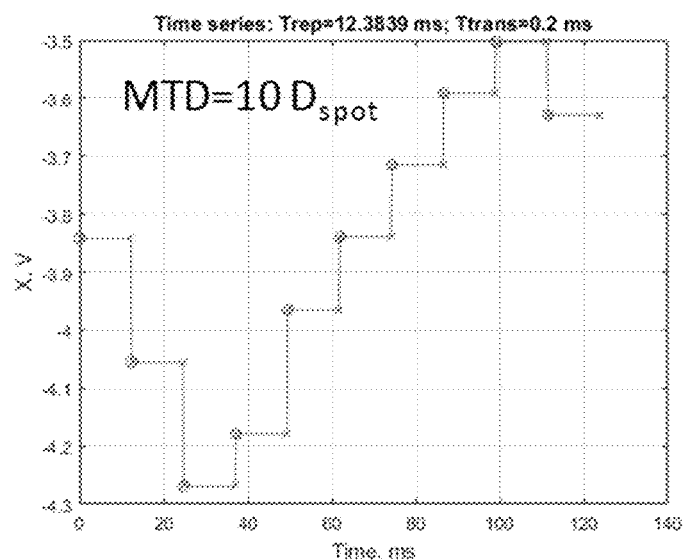
Figure 12C:
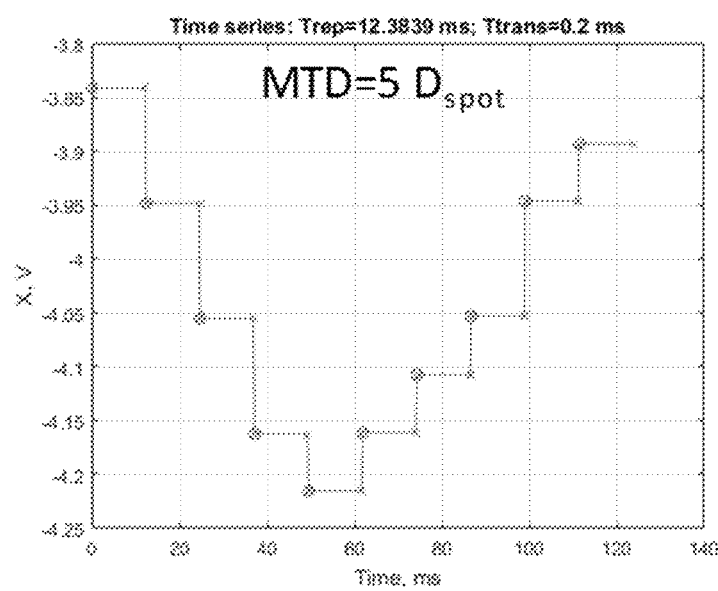

FIGS. 12A-C illustrate graphs for implementations of the treatment parameters shown in row B of FIG. 11 using a galvanometer mirror system (e.g., the galvanometer mirror system 312 shown in FIG. 3). Each graph shows the drive voltage applied to induce a tilt angle of the X mirror as a function of time as the treatment progresses. In particular, the mirror tilt angle is expressed in terms of the X voltage that controls the X mirror as described above. The mirror tilt angle remains fixed when a shot is delivered to a cell (during the shooting time) and varies as the galvanometer mirror system is adjusted to deliver a shot to the next cell (during the transit time). No photoactivating light is delivered to the galvanometer mirror system during the transit time. Practically, when the galvanometer mirror system is adjusted to deliver a shot to the next cell, a transient time is needed to allow the mirrors to stop moving. According to one approach, the laser beam is modulated and the galvanometer mirror system is synchronized so that photoactivating light is not delivered to the galvanometer mirror system during this transient time. FIG. 12A shows the tilt angle (X voltage) during the first ten shots of a treatment where travel distance is unconstrained, i.e., MTD=∞. FIG. 12B shows the tilt angle (X voltage) during the first ten shots of a treatment where travel distance is constrained to a travel distance of no greater than ten times the diameter $D_{sp}$ (100 µm), i.e., MTD=10 $D_{sp}$. FIG. 12C shows the tilt angle (X voltage) during the first ten shots of a treatment where travel distance is further constrained to a travel distance of no greater than five times the diameter $D_{sp}$ (100 µm), i.e., MTD=5 $D_{sp}$. FIGS. 12A-C demonstrate that constraining the travel distance to a few multiples of the laser spot size results in shorter travel distances between consecutive spots, i.e., smaller changes in tilt angle between spots.

Eye Motion Correction

As described above, the treatment system 300 shown in FIG. 3 includes an eye tracking system to account for motion of the eye 1 during treatment. According to some approaches, the position of the eye is monitored during treatment by processing images captured by an imaging system. In response, the treatment system dynamically adjusts the delivery of photoactivating light so that the pattern is applied to desired areas of the cornea.

Figure 13:
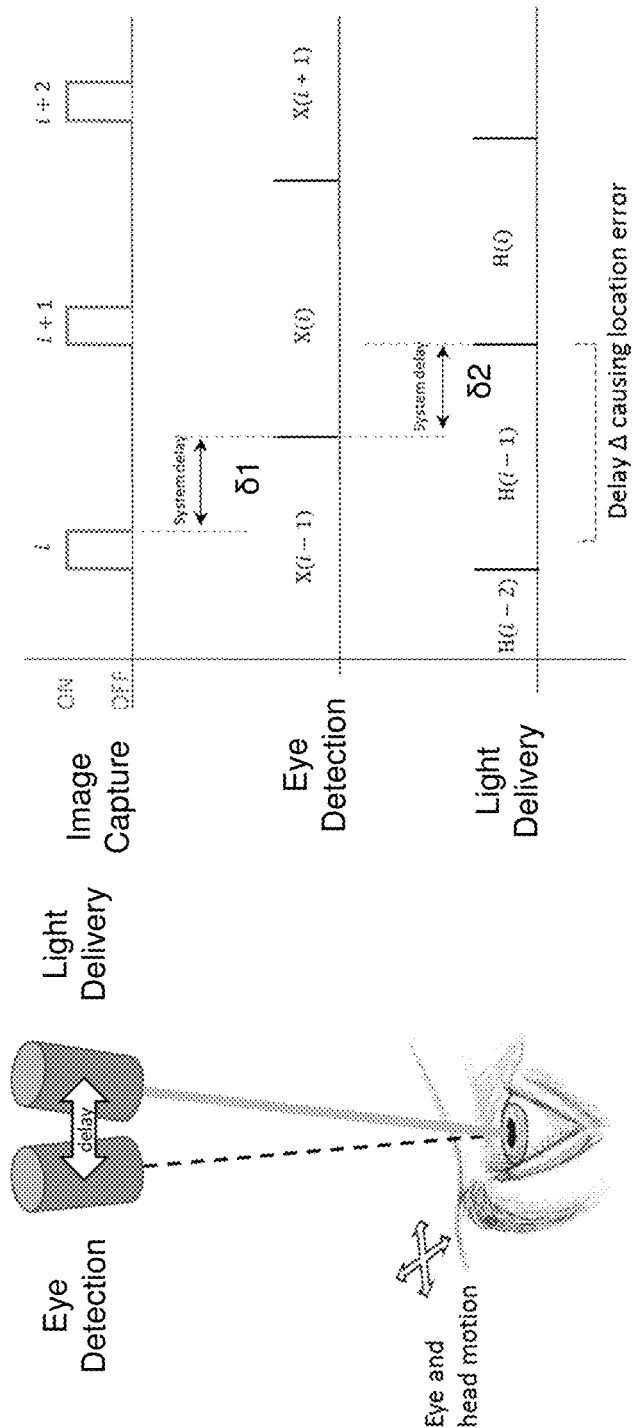
FIG. 13 illustrates a delay between eye position and delivery of photoactivating light due to discrete-time detection of the eye and finite response time of a treatment system, according to aspects of the present disclosure.

As shown in the timeline 1300 of FIG. 13, however, there is a delay between detection of the eye position and delivery of the photoactivating light due to discrete-time detection of the eye and finite response time of the treatment system. For instance, FIG. 13 shows that the imaging system captures an image i of the eye. The image i is processed and a position of the eye in image i is calculated to be X(i). The position X(i) is then processed to calculate the position of the desired treatment zone and photoactivating light H(i) is delivered to the desired treatment zone. The time required to process the image i results in a system delay of 61. Additionally, the time required to process the position X(i) and trigger delivery of the photoactivating light results in another system delay of 62. Thus, the total time A from the time that image i is captured to the time that photoactivating light is actually delivered is at least the sum of system delays 61 and 62. Accordingly, inaccuracies in the delivery of the photoactivating light may result if there is further eye movement during the delay time A.

Rapid eye movements, in particular, can cause location error in the delivery of the photoactivating light due to this delay. With the point and shoot approach above, the location error can be significant if the laser spot size is comparable to the amount of eye movement during the delay time. FIGS. 14(A)-(D) illustrate a grid 1406 defined by an arrangement of hexagonal cells 1407 for a grid-based point and shoot approach. As shown in FIG. 14(A), the treatment system intends to deliver a shot to a cell 1407a at time (i−Δ). An imaging system captures a series of frames from which the position of the eye and the relative location of the shot can be determined. In particular, FIGS. 14(B) and 14(C) illustrate consecutive frames at times i and (i+1), respectively. The frames show that the eye has moved and that the shot has been received by other unintended cells (location error). The grid 1406 is fixed relative to the eye and thus the location of the shot has moved relative to the grid 1406. As shown in FIG. 14(B), the shot is received across parts of cells 1407a-d at time i. Meanwhile, FIG. 14(C) shows that the shot is received across parts of cells 1407a, d, e at time (i+1).

Figure 14:
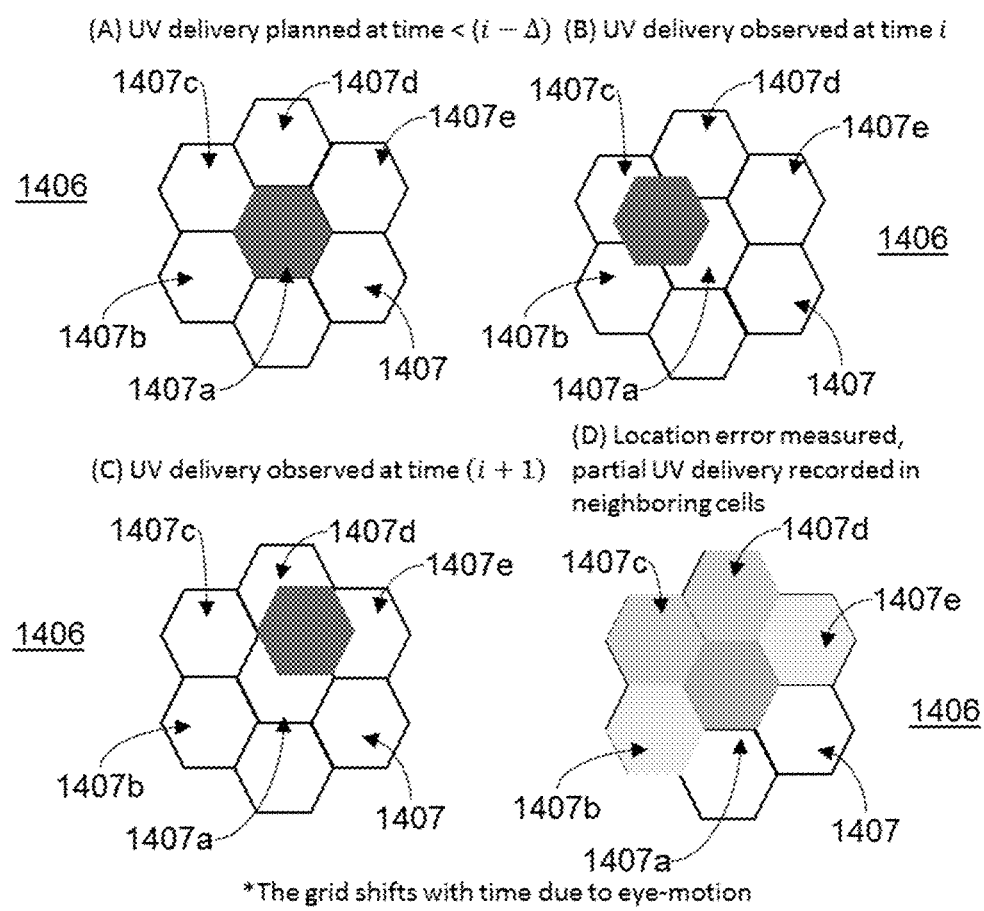
FIG. 14 illustrates an example approach for accounting for location error in a modified grid-based point and shoot approach, according to aspects of the present disclosure.

A motion model (e.g., linear model, Kalman filter, or FIR filter) is employed to model eye motion between consecutive frames and to determine the cells that receive photoactivating light between consecutive frames. The dose map can then be updated to indicate that each of such cells has received a dose of photoactivating light proportional to the area covered by the photoactivating light in the frames. Thus, as shown in FIG. 14(D), the dose map indicates that a dose of photoactivating light has been received by the cells 1407a-e based on the information in the frames at times i and (i+1). Moreover, as shown with the relative shading of the cells 1407a-e in FIG. 14(D), the dose map indicates the relative doses of photoactivating light that the cells 1407a-e have received. For instance, based on the total area of each cell 1407a-e covered by the photoactivating light in both frames, the cell 1407a has received the greatest dose, while the cells 1407c, d have received greater doses than the cells 1407b, e. The updated dose map can then be used to determine the location of the next shot as described above. Accordingly, FIG. 14 illustrates a modification of the grid-based point and shoot approach that employs the dose map to account for the effects of location error.

Although FIG. 14 illustrates modification of the grid-based point and shoot approach, other approaches for scanning photoactivating light across a cornea may include a similar mechanism whereby a dose map is dynamically updated to account for measured errors in delivery of photoactivating light and the scanning path is dynamically adjusted to spatially optimize applied doses during the treatment. Furthermore, in alternative embodiments, fluorescent signals resulting from the application of photoactivating light may be detected to determine the location of such application and account for eye motion as described above.

Lissajou Curve Scanning

Referring to the treatment system 300 of FIG. 3, the galvanometer mirror system 312 can be employed to create Lissajou curve scan patterns. Such scan patterns can be translated into independent mirror drive waveforms that cause the X mirror 312a and the Y mirror 312b to scan the laser beam in the x- and y-directions, respectively. For instance, each of the mirrors 312a, b can perform respective sine wave movements which can be described as:

$$x = X \sin(\omega_x t + \delta) \tag{26}$$

$$y = Y \sin(\omega_y t) \tag{27}$$

where X and Y correspond to the maximum laser beam movement on the eye surface.

As a specific example, when X=Y=A, $\omega_x=\omega_y=\omega$, and δ=90°, the Lissajou curve is a circle. The beam position and the scanning velocity at any moment can be described as $$s = x + jy = A \cos \omega t + jA \sin \omega t = Ae^{j\omega t} \tag{28}$$

$$\dot{s} = j\omega A e^{j\omega t} \tag{29}$$

In order to cover the entire scanning area, multiple scanning paths are involved. The amplitude A is a variable to fit the entire scanning area. In the case of uniform scanning speed:

$$\omega A = \text{constant} \tag{30}$$

Very dense Lissajou scanning paths may be employed to achieve proper cross-linking effect. The process of cross-linking in a region of corneal tissue requires a local supply of oxygen as well as cross-linking agent, e.g., riboflavin. As such, the cross-linking efficiency might decrease if consecutive scanning paths are too close to each other. To minimize a decrease in cross-linking efficiency, a scanning of n total paths can be interlaced by scanning the n total scan paths in a sequence defined by an interval m. For instance, if the scan pattern includes n=20 total scan paths (e.g., circular paths) and an interval m=5 is selected, the scan sequence can start with scan path 1 and proceeds to scan paths at every fifth interval after scan path 1, i.e., scan paths 6, 11, 16. The sequence can then move to scan path 2 and proceed to scan paths at every fifth interval after scan path 2, i.e., scan paths 7, 12, 17, and so on. The order for the total sequence is then scan paths 1, 6, 11, 16, 2, 7, 12, 17, 3, 8, 13, 18, 4, 9, 14, 19, 5, 10, 15, 20. Alternatively, a sequence can start with scan path 20 and proceed in reverse to scan paths at every fifth interval, i.e., the order for the total sequence is scan paths 20, 15, 10, 5, 19, 14, 9, 4, 18, 13, 8, 3, 17, 12, 7, 2, 16, 11, 6, 1.

The scanning of each path can start at any portion of the path. For instance, if circular paths are scanned according to the previous sequence, scanning of paths 20, 15, 10, 5 can start at 45° on the circles; scanning of paths 19, 14, 9, 4 can start from at 40° on the circles; scanning of paths 18, 13, 8, 3 can start at 35° on the circles; and so on. Because the scan pattern for the entire treatment may involve a large number of scan paths, many start angles may be employed to achieve a uniform distribution of start angles.

Dead Zone Dwelling

In some cases, very high linear scanning speed might be employed for effective cross-linking. For instance, if linear scanning speed is 3.14 mm/ms, a 0.1 mm diameter scanning circle is completed in 0.1 ms and the galvanometer function frequency $\omega$ is 10 kHz. This function frequency is very difficult to achieve with most commercially available galvanometer mirror systems. Indeed, it is common practice to apply one or more notch filters on a galvanometer servo board to avoid issues associated with resonance in that range. As such, there is a scanning dead zone due to the limitations of conventional galvanometer performance. Moreover, this dead zone may create issues for achieving peak power for the photoactivating light for cross-linking treatment.

The laser beam, however, can move into the dead zone and stay (dwell) in the dead zone for a short period of time when, for each scan path, the laser beam scans the portion closest to the dead zone. For instance, if a cross-linking treatment lasts for a total of 1000 seconds and scans interlaced paths (e.g., circular scan paths) ten times for each scan pattern at 10 Hz repetition frequency, there are 100,000 opportunities to move into the dead zone. If the dead zone size is one percent of the total scanning area, the total dwelling time may be 10 seconds, and 100 μs for each move into the dead zone (dwelling).

Uniform dead zone dwelling positions can be generated with deterministic equations, but dead zone dwelling can also be achieved randomly. For instance, with two 0 to 1 uniformly distributed numbers $r_1$ and $r_2$, and dead zone radius is R, random dead zone dwelling position may be:

$$x = R\sqrt{r_1} \cos(2\pi r_2) \tag{31}$$

$$y = R\sqrt{r_1} \sin(2\pi r_2) \tag{32}$$

Laser Power Control and Synchronization

Laser power is synchronized with laser beam position during cross-linking treatments. Additionally, synchronizing a laser modulation signal with a position sensor may be employed to maintain precise control over the temporal and spatial characteristics of the scan pattern.

Such synchronization may be necessary because a scan pattern, e.g., with Lissajous scan paths, may not correspond exactly with the desired treatment area. For instance, the scan pattern may be defined by a circular boundary and circular scan paths, but the zone for cross-linking treatment may not be correspondingly circular. As such, it may be necessary to turn the laser power on when the laser beam is inside the treatment zone and to turn the laser power off when the laser beam is outside the treatment zone. Such synchronization may also be necessary because non-uniform laser power is needed for portions of the treatment zone.

Modulated CW laser output power can be manipulated via triggering signals from an acousto-optic modulator or an electro-optic modulator, manipulated directly via diode current, etc. A time delay, also known as rise and fall time, generally occurs when the laser is turned on or off. High quality synchronization accounts for this time delay via calibration.

The triggering signals for modulation of laser output power can be provided via an open or closed loop control system. A closed loop control system employs a feedback signal for position. An open loop control system involves careful pre-calibration of time delay associated with the triggering signal.

TTL (Transistor-Transistor Logic) generally involves a short rise and fall time and may be employed for digital modulation. Other differential signaling such as PECL (Positive Emitter coupled Logic), LV-PECL (Low-Voltage Positive Emitter coupled Logic), and LVDS (Low-Voltage Differential Signaling) are also able to modulate at high frequencies with minimal noise.

Stochastic Model, Estimation, and Control for Eye Tracking

Kalman Filter

An algorithm based on the Kalman filter may be employed to remove errors from eye tracking measurements. The Kalman filter is a set of mathematical equations that implement a predictor-corrector type of estimator for a stochastic system. It is optimal in the sense of minimizing the estimated error when some presumed conditions are met. With the Kalman filter, eye tracking accuracy can be significantly improved, in contrast to approaches that use direct measurements of eye position. Such eye tracking can effectively estimate eye movement with a regular position-velocity-acceleration component and occasional random component. To implement such eye tracking in a two-dimensional space, two independent filters are employed, i.e., one filter for each spatial dimension.

State-Space Model for Kalman Filter

The Kalman filter addresses the general problem of estimating the state $x \in R^n$ of a discrete-time controlled process that is governed by the linear stochastic difference equation:

$$x_k = A x_{k-1} + B u_k + w_{k-1} \tag{33}$$

With the measurement $z \in R^m$, $$z_k = H x_k + v_k \tag{34}$$

The random variables $w_k$ and $v_k$ represent the process and measurement noise. They are assumed to be independent, with normal probability distribution:

$$p(w) \sim N(0, Q) \tag{35}$$

$$p(v) \sim N(0, R) \tag{36}$$

One defines $\hat{x}_k^- \in R^n$ to be a priori state estimate at step k given knowledge of the process prior to step k, and $\hat{x}_k \in R^n$ to be a posteriori state estimate at step k given measurement $z_k$. One can then define a priori and a posteriori estimate errors as $e_k^- \equiv x_k - \hat{x}_k^-$ and $e_k \equiv x_k - \hat{x}_k$. The priori and posteriori estimate error covariances are:

$$P_k^- = E[e_k^- e_k^{-T}] \quad (37)$$

$$P_k = E[e_k e_k^T] \quad (38)$$

Discrete Kalman Filter Algorithm

The equations of Kalman filter fall into two groups: time update equations and measurement update equations:

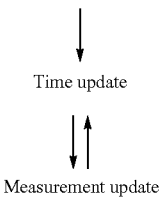

Initial estimates for $\hat{x}_{k-1}$ and $P_{k-1}$

Time update

Measurement update

The time update equations are responsible for projecting forward the current state and error covariance estimates to obtain a priori estimates of the next time step:

Project the state ahead: $\hat{x}_k^- = A\hat{x}_{k-1} + Bu_k$ (39)

Project the error covariance: $P_k^- = AP_{k-1}A^T + Q$ (40)

The measurement update equations are responsible for the feedback. They incorporate a new measurement into the a priori estimate to obtain an improved a posteriori estimate.

Compute the Kalman gain: $K_k = P_k^- H^T (HP_k^- H^T + R)^{-1}$ (41)

Update estimate with measurement: $\hat{x}_k = \hat{x}_k^- + K_k(z_k - H\hat{x}_k^-)$ (42)

Update the error covariance: $P_k = (I - K_k H) P_k^-$ (43)

Raster Scan with Polygon Scanner

Figure 15:
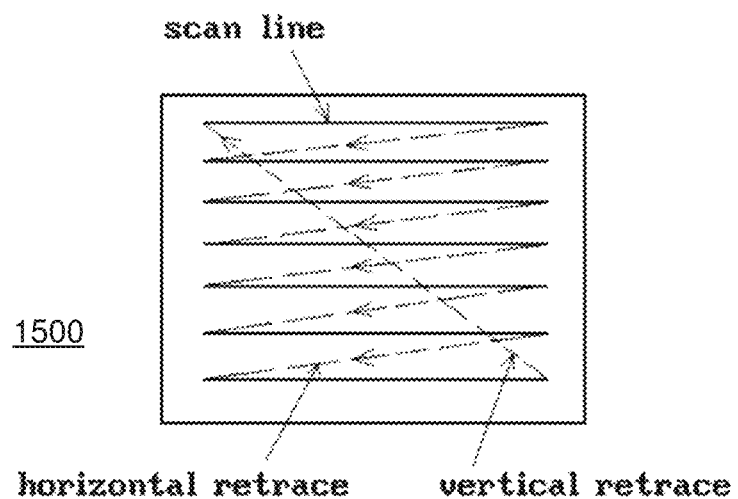
FIG. 15 illustrates an example raster scanning pattern, according to aspects of the present disclosure.

FIG. 15 illustrates an example raster scan pattern 1500. In raster scanning, a laser beam, starting at the top line, sweeps horizontally left-to-right at a steady speed, then rapidly moves back to the left, where it can sweep out the next line. Meanwhile, the vertical position of the laser beam moves steadily downward. The movement can be either continuous or intermittent. When the scan path is complete, the laser beam can start from the top line or start from a position between the first line and second line to do an interlaced scan. With raster scanning, laser modulation is synchronized with the cross-linking treatment area, as described above.

A polygon scan can typically run faster because there is no dead zone as with a Lassajou curve scan. The vertical movement of a raster scan is much slower, and it can be implemented with simple, slow scanning, e.g., MEMS-based scanning.

Zig-Zag Scan with Resonant Scanner

Figure 16:
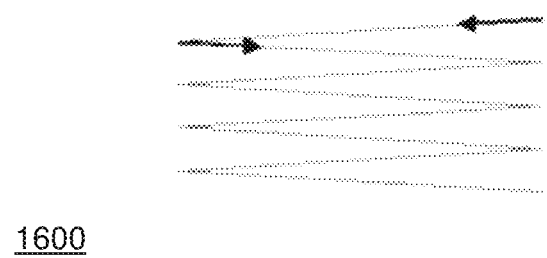
FIG. 16 illustrates an example zig-zag scanning pattern, according to aspects of the present disclosure.

FIG. 16 illustrates an example zig-zag scan pattern 1600. Similar to raster scan, zig-zag scanning as shown in FIG. 16 involves faster horizontal scanning and slower vertical scanning. Zig-zag scanning can sweep horizontally in both directions. The vertical movement can be either continuous or intermittent. Zig-zag scanning can be implemented with a resonant scanner. With zig-zag scanning, laser modulation is synchronized with the cross-linking treatment area, as described above.

Alternative Laser Treatment Systems

As described above, using a laser light source to deliver a photoactivating light pattern can provide benefits for corneal cross-linking treatments over approaches that employ a LED light source. LED light sources may provide light beams of lower optical quality, including low coherence, poor collimation, and/or large diameters. With light beams of such low quality, the choice of available patterns for the delivery of photoactivating light may be more limited and may require more complex and expansive aspherical optics for pattern formation.

Figure 17:
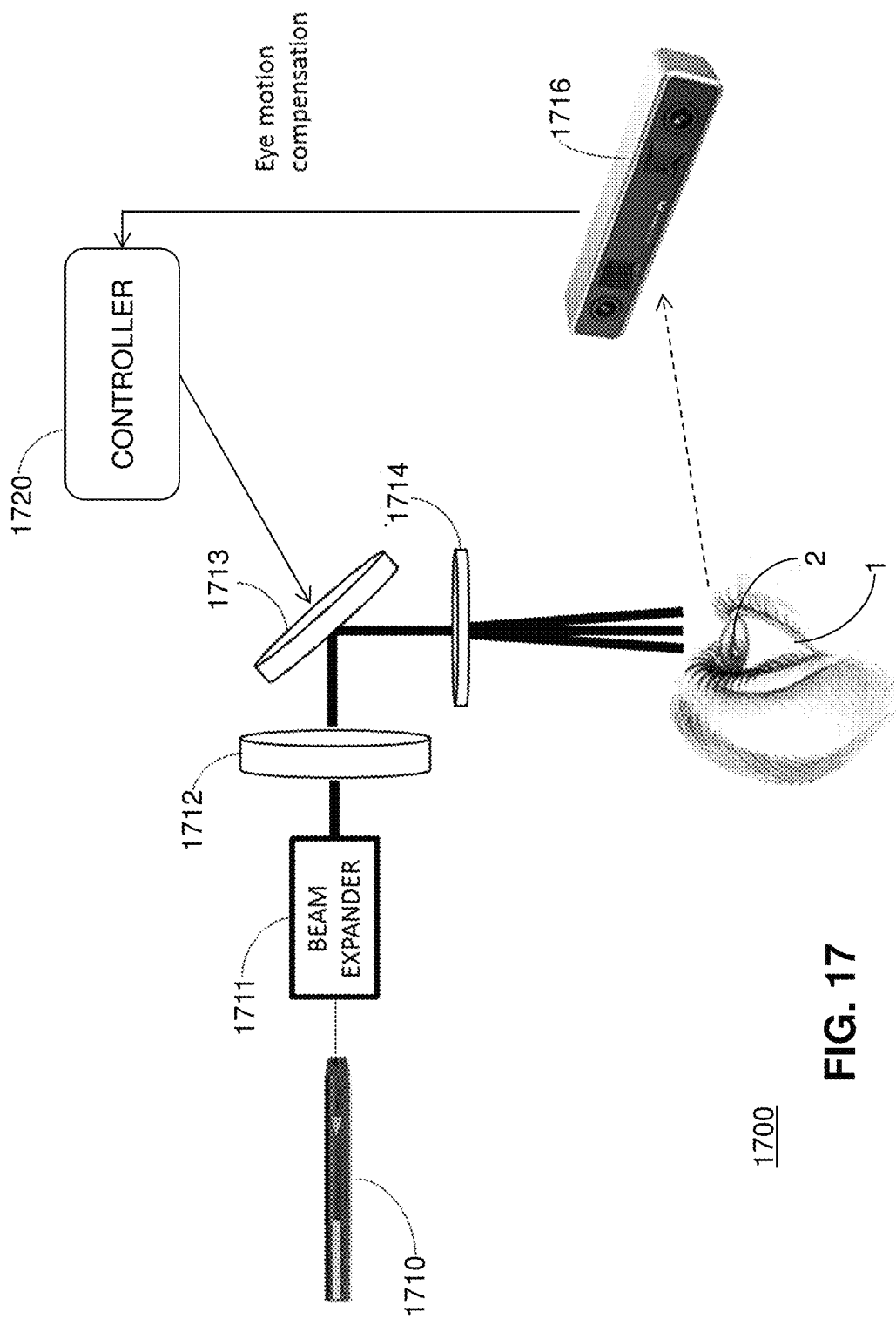
FIG. 17 illustrates an example treatment system that provides a laser-based approach for projecting patterns of photoactivating light to a cornea employing a diffractive multi-beam splitter, according to aspects of the present disclosure.
Figure 18:
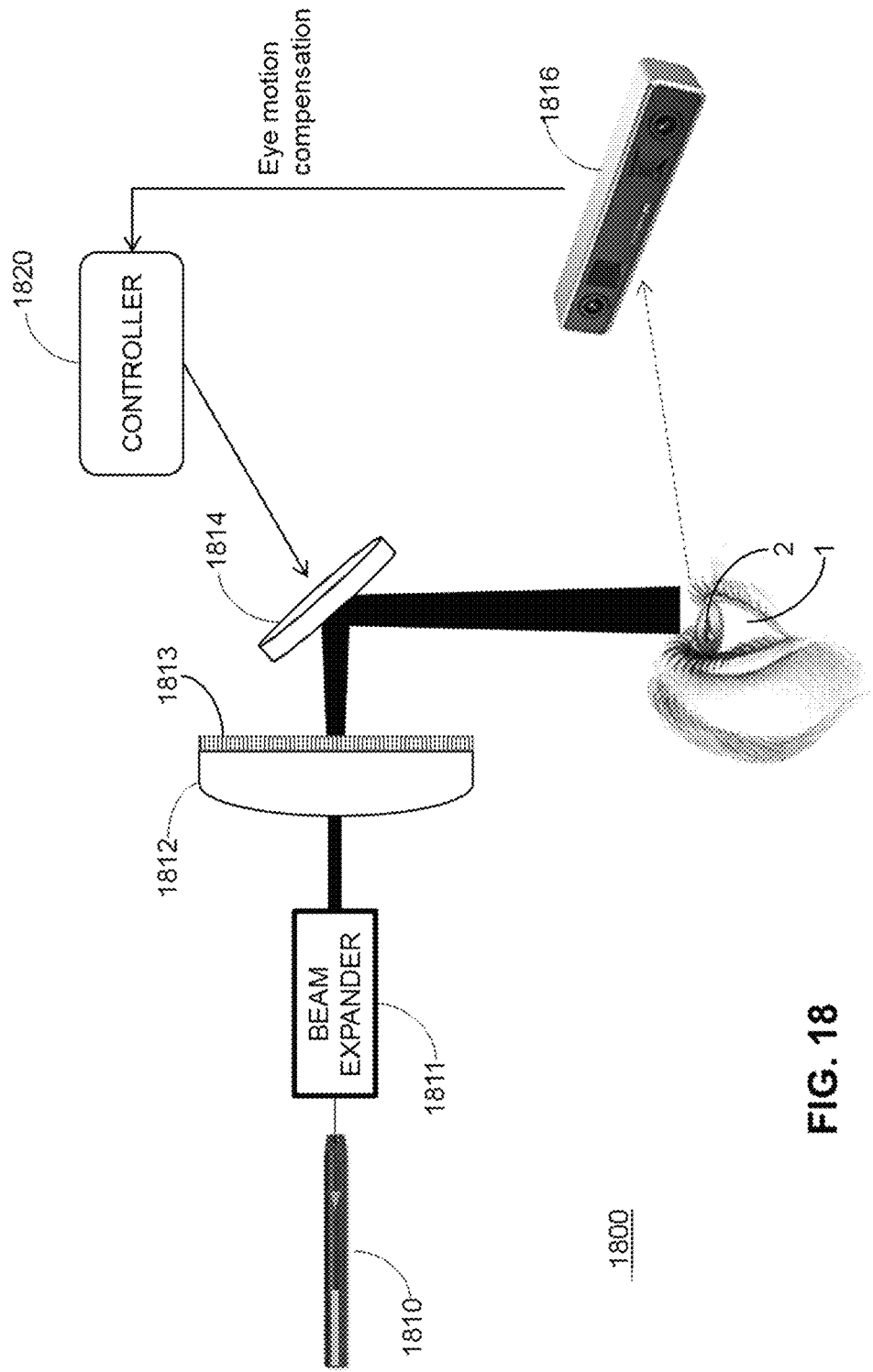
FIG. 18 illustrates an example treatment system that provides a laser-based approach for projecting patterns of photoactivating light to a cornea employing a diffractive beam shaper, according to aspects of the present disclosure.

In addition to the laser-based approaches employing XY scanners as described above, FIGS. 17 and 18 illustrate examples of other treatment systems that provide other laser-based approaches for projecting patterns of photoactivating light to a cornea. In particular, FIG. 17 illustrates an example treatment system 1700 that employs a diffractive multi-beam splitter, and FIG. 18 illustrates an example treatment system 1800 that employs a diffractive beam shaper. These treatment systems may be more efficient for the use of single-mode lasers.

The treatment system 1700 shown in FIG. 17 includes a UV (e.g., UVA) laser source 1710, a beam expander 1711, a two-dimensional beam splitter 1712, a laser beam deflector 1713, and a focusing lens 1714. The laser source 1710 may be implemented with a light amplitude modulator (either internal or external to the laser source 1710). The laser beam from the laser source 1710 is directed to the beam expander 1711 and the resulting expanded beam is directed to the two-dimensional beam splitter 1712 (e.g., a diffractive beam splitter), which generates more than one laser beam spot. The laser beam deflector 1713 receives and directs the laser beam spots to the focusing lens 1714, which projects a pattern of the laser beam spots to the cornea 2. The spot pattern is generated from the laser beam spots at the surface of the cornea 2 with a pattern size that is determined by the distance from the cornea 2 to the focusing lens 1714. The cross-linking activity occurs simultaneously at all spots using either continuous and/or pulsing laser light.

The treatment system 1700 includes a controller 1720 that may control aspects of the treatment system 1700. Additionally, the treatment system 1700 includes an imaging system 1716 (e.g., a camera) that captures images of the eye 1. The controller 1720 can receive and process the images from the imaging system 1716 to determine the position of the cornea 2 relative to the treatment system 1700. To compensate for changes in the position of the cornea 2, the controller 1720 can control the laser beam deflector 1713 to adjust the scanned laser beam and cause the spot pattern to be applied to the desired areas of the cornea 2. As such, the imaging system 1716 and the controller 1720 combine to provide an eye tracking system.

Meanwhile, the treatment system 1800 shown in FIG. 18 includes a UV (e.g., UVA) laser source 1810, a beam expander 1811, a focusing lens 1812, a diffractive beam shaper 1813, and a laser beam deflector 1814. The laser source 1810 may be implemented with a light amplitude modulator (either internal or external to the laser source 1810). The laser beam from the laser source 1810 is directed to the beam expander 1811 and the resulting expanded beam is directed to the focusing lens 1812 and the diffractive beam shaper 1813 (e.g., flattop generator, ring generator, or custom shape generator). The laser beam deflector 1814 receives and directs the laser beam from the diffractive beam shaper 1813 to the cornea 2. As such, a laser beam spot of desired size and shape is generated at the surface of the cornea 2. Further embodiments may optionally employ additional lenses and beam shaper devices.

Like the treatment system 1700, the treatment system 1800 includes a controller 1820 that may control aspects of the treatment system 1800. Additionally, the treatment system 1800 includes an imaging system 1816 (e.g., a camera) that captures images of the eye 1. The controller 1820 can receive and process the images from the imaging system 1816 to determine the position of the cornea 2 relative to the treatment system 1800. To compensate for changes in the position of the cornea 2, the controller 1820 can control the laser beam deflector 1814 to adjust the scanned laser beam and cause the spot pattern to be applied to the desired areas of the cornea 2. As such, the imaging system 1816 and the controller 1820 combine to provide an eye tracking system.

In general, cross-linking treatment systems employing a laser light source can deliver more sophisticated and sharper photoactivating light patterns. As described above, embodiments can employ XY scanners, diffractive multi-beam splitters, and diffractive beam shapers to achieve the desired patterns.

As also described above, photoactivating light patterns from laser-based treatment systems can be optimized to achieve clinical efficacy and a desired treatment objective (e.g., refractive correction) based on particular eye parameters for individual subjects. Optimized laser-based treatment system can precisely control the shape of a treatment zone and local strength for a patient-specific treatment pattern. Advantageously, optimized laser-based treatment systems can enhance cross-linking by efficiently use cross-linking agent and ambient oxygen based on photochemical kinetic reactions. Indeed, such treatment systems can make it unnecessary to have hyperoxic condition during treatment, i.e., an external gas source, treatment masks, etc. are not required to supply supplemental concentrated oxygen.

As described above, according to some aspects of the present disclosure, some or all of the steps of the above-described and illustrated procedures can be automated or guided under the control of a controller. Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA), application specific integrated circuits (ASIC), or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), application specific integrated circuits (ASIC), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A system for treating an eye, comprising:
   a laser light source configured to provide photoactivating light;
   a scanning mirror system configured to receive the photoactivating light as a laser beam and to move the laser beam over a cornea treated with a cross-linking agent; and
   a controller configured to provide control signals to programmatically control the laser light source and the scanning mirror system, the one or more control signals causing the laser beam to visit one or more regions of the cornea more than once according to a scan pattern and expose the one or more regions to the photoactivating light, wherein the photoactivating light causes the cross-linking agent in the one or more exposed regions to react with oxygen to generate cross-linking activity in the one or more exposed regions, wherein the one or more control signals programmatically control the laser light source, such that a predetermined period of time passes between visits by the laser beam to the one or more exposed regions, and wherein the scan pattern includes unexposed regions on all four sides of each exposed region, such that the scan pattern is a spiraled checkerboard having exposed regions that are smaller in size the closer a particular exposed region is to a center of the scan pattern.

2. The system of claim 1, wherein the light source is operable to adjust a power associated with the laser beam, and the scan pattern is optimized according to the power associated with the laser beam.

3. The system of claim 1, wherein the scanning mirror system is operable to adjust a speed of the laser beam as the laser beam moves over the cornea, and the scan pattern is optimized according to the speed of the laser beam.

4. The system of claim 1, further comprising one or more optical elements configured to receive the photoactivating light and determine a spot size associated with the laser beam, wherein the scan pattern is optimized according to the spot size associated with the laser beam.

5. The system of claim 1, wherein the scanning mirror system includes a galvanometer pair, the galvanometer pair including a first mirror configured to move the laser beam along a first axis and a second mirror configured to move the laser beam along a second axis.

6. The system of claim 1, wherein the scan pattern causes the laser beam to visit the one or more exposed regions while keeping one or more adjacent regions unexposed to the photoactivating light, and the one or more adjacent unexposed regions provide oxygen for diffusion into the one or more exposed regions.

7. The system of claim 1, wherein the scan pattern is defined by a pulsing of the laser beam according to a duty cycle, wherein, as the scanning mirror system scans the laser beam over the cornea, the pulsing causes the laser beam to visit the one or more exposed regions when the laser beam is on during the duty cycle while adjacent regions are unexposed to the photoactivating light when the laser beam is off during the duty cycle, and the adjacent unexposed regions provide oxygen for diffusion into the one or more exposed regions.

8. The system of claim 7, wherein the pulsing of the laser beam has a frequency that varies according to a position of the laser beam in the scan pattern.

9. The system of claim 1, wherein the one or more exposed regions correspond to a plurality of discrete dots defining the scan pattern.

10. A method for treating an eye, comprising:
generating photoactivating light with a laser light source;
directing the photoactivating light as a laser beam to a scanning mirror system;
operating the scanning mirror system to cause the laser beam to move over a cornea and visit one or more regions of the cornea more than once according to a scan pattern and expose the one or more regions to the photoactivating light, wherein the photoactivating light causes a cross-linking agent in the one or more exposed regions to react with oxygen to generate cross-linking activity in the one or more exposed regions, optimizing the scan pattern by programmatically controlling the laser light source, such that a predetermined period of time passes between visits by the laser beam to the one or more exposed regions, and wherein the scan pattern includes unexposed regions on all four sides of each exposed region, such that the scan pattern is a spiraled checkerboard having exposed regions that are smaller in size the closer a particular exposed region is to a center of the scan pattern.

11. The method of claim 10, wherein optimizing the scan pattern includes adjusting a power associated with the laser beam.

12. The method of claim 10, wherein optimizing the scan pattern includes adjusting a speed of the laser beam, and the scan pattern is optimized according to the speed of the laser beam.

13. The method of claim 10, wherein optimizing the scan pattern includes determining a spot size associated with the laser beam.

14. The method of claim 10, wherein the scanning mirror system includes a galvanometer pair, the galvanometer pair including a first mirror configured to move the laser beam along a first axis and a second mirror configured to move the laser beam along a second axis.

15. The method of claim 10, wherein optimizing the scan pattern includes defining the scan pattern to cause the laser beam to visit the one or more exposed regions while keeping one or more adjacent regions unexposed to the photoactivating light, the one or more adjacent unexposed regions provide oxygen for diffusion into the one or more exposed regions.

16. The method of claim 10, wherein optimizing the scan pattern includes defining the scan pattern to pulse the laser beam according to a duty cycle, wherein, as the scanning mirror system scans the laser beam over the cornea, the pulsing causes the laser beam to visit the one or more exposed regions when the laser beam is on during the duty cycle while adjacent regions are unexposed to the photoactivating light when the laser beam is off during the duty cycle, the adjacent unexposed regions provide oxygen for diffusion into the one or more exposed regions.

17. The method of claim 16, wherein the pulsing of the laser beam has a frequency that varies according to a position of the laser beam in the scan pattern.

18. The method of claim 10, wherein the one or more exposed regions correspond to a plurality of discrete dots defining the scan pattern.

\* \* \* \* \*